(12) United States Patent
Stigall

(10) Patent No.: US 10,238,367 B2
(45) Date of Patent: Mar. 26, 2019

(54) DEVICES, SYSTEMS, AND METHODS FOR TARGETED CANNULATION

(71) Applicant: Volcano Corporation, San Diego, CA (US)

(72) Inventor: Jeremy Stigall, Carlsbad, CA (US)

(73) Assignee: VOLCANO CORPORATION, San Diego, CA (US)

( * ) Notice: Subject to any disclaimer, the term of this patent is extended or adjusted under 35 U.S.C. 154(b) by 210 days.

(21) Appl. No.: 14/103,507

(22) Filed: Dec. 11, 2013

(65) Prior Publication Data

US 2014/0171788 A1     Jun. 19, 2014

Related U.S. Application Data

(60) Provisional application No. 61/737,022, filed on Dec. 13, 2012, provisional application No. 61/737,040, filed on Dec. 13, 2012.

(51) Int. Cl.
    *A61B 17/34*     (2006.01)
    *A61B 8/08*     (2006.01)
    (Continued)

(52) U.S. Cl.
    CPC ............ *A61B 8/488* (2013.01); *A61B 8/085* (2013.01); *A61B 8/0833* (2013.01);
    (Continued)

(58) Field of Classification Search
None
See application file for complete search history.

(56) References Cited

U.S. PATENT DOCUMENTS 3,301,258 A    1/1967    Werner
3,556,079 A    1/1971    Izumi-Otsu
(Continued)

FOREIGN PATENT DOCUMENTS

EP          1041373 A2    10/2000
EP         01172637 A1    1/2002
(Continued)

OTHER PUBLICATIONS

International Search Report and Written Opinion received in Patent Cooperation Treaty Application No. PCT/US2013/074171, dated Mar. 28, 2014, 15 pages.
(Continued)

*Primary Examiner* — Thomas Hong
*Assistant Examiner* — Marjan Saboktakin

(57) ABSTRACT

Described herein is a sensing wire for locating a blood vessel in a patient. The sensing wire comprises a hollow, rigid tube including a lumen extending from a proximal portion to a distal portion, an ultrasonic sensor coupled to the distal portion of the tube, and a communication assembly positioned at the distal portion and coupled to the ultrasound sensor. Also described is a system for accessing and evaluating a blood vessel in a patient. The system comprises an access sensor wire, an access needle sized to receive the access sensor wire, and a second sensing wire configured to be positioned within the access needle. A method is also disclosed for accessing a blood vessel with an introduction needle, where a short access sensing wire is replaced by a much longer second sensing wire after the needle is positioned in the vessel.

14 Claims, 12 Drawing Sheets

(51) Int. Cl.
*A61B 8/12* (2006.01)
*A61B 8/00* (2006.01)
*A61B 90/00* (2016.01)

(52) U.S. Cl.
CPC .............. *A61B 8/0891* (2013.01); *A61B 8/12* (2013.01); *A61B 8/4444* (2013.01); *A61B 17/3403* (2013.01); *A61B 8/0841* (2013.01); *A61B 8/445* (2013.01); *A61B 17/3417* (2013.01); *A61B 2017/3413* (2013.01); *A61B 2090/3784* (2016.02)

(56) References Cited

U.S. PATENT DOCUMENTS

| | | | |
|---|---|---|---|
| 3,617,880 A | 11/1971 | Cormack et al. | |
| 3,789,841 A | 2/1974 | Antoshkiw | |
| 3,841,308 A | 10/1974 | Tate | |
| 4,140,364 A | 2/1979 | Yamashita et al. | |
| 4,274,423 A | 6/1981 | Mizuno et al. | |
| 4,344,438 A | 8/1982 | Schultz | |
| 4,398,791 A | 8/1983 | Dorsey | |
| 4,432,370 A | 2/1984 | Hughes et al. | |
| 4,552,554 A | 11/1985 | Gould et al. | |
| 4,577,543 A | 3/1986 | Wilson | |
| 4,582,067 A * | 4/1986 | Silverstein | A61B 1/015 600/455 |
| 4,676,980 A | 6/1987 | Segal et al. | |
| 4,682,895 A | 7/1987 | Costello | |
| 4,733,665 A | 3/1988 | Palmaz | |
| 4,744,619 A | 5/1988 | Cameron | |
| 4,762,129 A | 8/1988 | Bonzel | |
| 4,766,386 A | 8/1988 | Oliver et al. | |
| 4,771,774 A | 9/1988 | Simpson et al. | |
| 4,794,931 A | 1/1989 | Yock | |
| 4,800,886 A | 1/1989 | Nestor | |
| 4,803,639 A | 2/1989 | Steele et al. | |
| 4,816,567 A | 3/1989 | Cabilly et al. | |
| 4,819,740 A | 4/1989 | Warrington | |
| 4,821,731 A | 4/1989 | Martinelli et al. | |
| 4,824,435 A | 4/1989 | Giesy et al. | |
| 4,830,023 A | 5/1989 | de Toledo et al. | |
| 4,834,093 A | 5/1989 | Littleford et al. | |
| 4,841,977 A | 6/1989 | Griffith et al. | |
| 4,864,578 A | 9/1989 | Proffitt et al. | |
| 4,873,690 A | 10/1989 | Adams | |
| 4,877,314 A | 10/1989 | Kanamori | |
| 4,887,606 A | 12/1989 | Yock et al. | |
| 4,917,085 A | 4/1990 | Smith | |
| 4,917,097 A | 4/1990 | Proudian et al. | |
| 4,928,693 A | 5/1990 | Goodin et al. | |
| 4,932,413 A | 6/1990 | Shockey et al. | |
| 4,932,419 A | 6/1990 | de Toledo | |
| 4,948,229 A | 8/1990 | Soref | |
| 4,951,677 A | 8/1990 | Crowley et al. | |
| 4,969,742 A | 11/1990 | Falk et al. | |
| 4,987,412 A | 1/1991 | Vaitekunas et al. | |
| 4,993,412 A | 2/1991 | Murphy-Chutorian | |
| 4,998,972 A | 3/1991 | Chin et al. | |
| 5,000,185 A | 3/1991 | Yock | |
| 5,024,234 A | 6/1991 | Leary et al. | |
| 5,025,445 A | 6/1991 | Anderson et al. | |
| 5,032,123 A | 7/1991 | Katz et al. | |
| 5,037,169 A | 8/1991 | Chun | |
| 5,039,193 A | 8/1991 | Snow et al. | |
| 5,040,548 A | 8/1991 | Yock | |
| 5,041,108 A | 8/1991 | Fox et al. | |
| 5,054,492 A | 10/1991 | Scribner et al. | |
| 5,065,010 A | 11/1991 | Knute | |
| 5,065,769 A | 11/1991 | de Toledo | |
| 5,085,221 A | 2/1992 | Ingebrigtsen et al. | |
| 5,095,911 A | 3/1992 | Pomeranz | |
| 5,100,424 A | 3/1992 | Jang et al. | |
| 5,120,308 A | 6/1992 | Hess | |
| 5,125,137 A | 6/1992 | Corl et al. | |
| 5,135,486 A | 8/1992 | Eberle et al. | |
| 5,135,516 A | 8/1992 | Sahatjian et al. | |
| 5,155,439 A | 10/1992 | Holmbo et al. | |
| 5,158,548 A | 10/1992 | Lau et al. | |
| 5,163,445 A | 11/1992 | Christian et al. | |
| 5,167,233 A | 12/1992 | Eberle et al. | |
| 5,174,295 A | 12/1992 | Christian et al. | |
| 5,176,141 A | 1/1993 | Bom et al. | |
| 5,176,674 A | 1/1993 | Hofmann | |
| 5,178,159 A | 1/1993 | Christian | |
| 5,183,048 A | 2/1993 | Eberle | |
| 5,188,632 A | 2/1993 | Goldenberg | |
| 5,201,316 A | 4/1993 | Pomeranz et al. | |
| 5,202,745 A | 4/1993 | Sorin et al. | |
| 5,203,779 A | 4/1993 | Muller et al. | |
| 5,220,922 A | 6/1993 | Barany | |
| 5,224,953 A | 7/1993 | Morgentaler | |
| 5,226,421 A | 7/1993 | Frisbie et al. | |
| 5,240,003 A | 8/1993 | Lancee et al. | |
| 5,240,437 A | 8/1993 | Christian | |
| 5,242,460 A | 9/1993 | Klein et al. | |
| 5,243,988 A | 9/1993 | Sieben et al. | |
| 5,257,974 A | 11/1993 | Cox | |
| 5,259,385 A * | 11/1993 | Miller | A61B 8/12 600/453 |
| 5,266,302 A | 11/1993 | Peyman et al. | |
| 5,267,954 A | 12/1993 | Nita | |
| 5,301,001 A | 4/1994 | Murphy et al. | |
| 5,309,915 A | 5/1994 | Ember | |
| 5,311,871 A * | 5/1994 | Yock | A61B 8/0833 600/461 |
| 5,312,425 A | 5/1994 | Evans et al. | |
| 5,313,949 A | 5/1994 | Yock | |
| 5,313,957 A | 5/1994 | Little | |
| 5,319,492 A | 6/1994 | Dorn et al. | |
| 5,321,501 A | 6/1994 | Swanson et al. | |
| 5,325,198 A | 6/1994 | Hartley et al. | |
| 5,336,178 A | 8/1994 | Kaplan et al. | |
| 5,346,689 A | 9/1994 | Peyman et al. | |
| 5,348,017 A | 9/1994 | Thornton et al. | |
| 5,348,481 A | 9/1994 | Ortiz | |
| 5,353,798 A | 10/1994 | Sieben | |
| 5,358,409 A | 10/1994 | Obara | |
| 5,358,478 A | 10/1994 | Thompson et al. | |
| 5,368,037 A | 11/1994 | Eberle et al. | |
| 5,373,845 A | 12/1994 | Gardineer et al. | |
| 5,373,849 A | 12/1994 | Maroney et al. | |
| 5,375,602 A | 12/1994 | Lancee et al. | |
| 5,377,682 A | 1/1995 | Ueno et al. | |
| 5,383,853 A | 1/1995 | Jung et al. | |
| 5,387,193 A | 2/1995 | Miraki | |
| 5,396,328 A | 3/1995 | Jestel et al. | |
| 5,397,355 A | 3/1995 | Marin et al. | |
| 5,405,377 A | 4/1995 | Cragg | |
| 5,411,016 A | 5/1995 | Kume et al. | |
| 5,419,777 A | 5/1995 | Hofling | |
| 5,421,338 A | 6/1995 | Crowley et al. | |
| 5,423,806 A | 6/1995 | Dale et al. | |
| 5,427,108 A | 6/1995 | Bollinger | |
| 5,427,118 A | 6/1995 | Nita et al. | |
| 5,431,673 A | 7/1995 | Summers et al. | |
| 5,436,759 A | 7/1995 | Dijaili et al. | |
| 5,439,139 A | 8/1995 | Brovelli | |
| 5,443,457 A | 8/1995 | Ginn et al. | |
| 5,453,575 A | 9/1995 | O'Donnell et al. | |
| 5,456,693 A | 10/1995 | Conston et al. | |
| 5,459,570 A | 10/1995 | Swanson et al. | |
| 5,480,388 A | 1/1996 | Zadini et al. | |
| 5,485,845 A | 1/1996 | Verdonk et al. | |
| 5,492,125 A | 2/1996 | Kim et al. | |
| 5,496,997 A | 3/1996 | Pope | |
| 5,507,761 A | 4/1996 | Duer | |
| 5,512,044 A | 4/1996 | Duer | |
| 5,514,128 A | 5/1996 | Hillsman et al. | |
| 5,529,674 A | 6/1996 | Hedgcoth | |
| 5,541,730 A | 7/1996 | Chaney | |
| 5,546,717 A | 8/1996 | Penczak et al. | |
| 5,546,948 A | 8/1996 | Hamm et al. | |
| 5,565,332 A | 10/1996 | Hoogenboom et al. | |
| 5,573,520 A | 11/1996 | Schwartz et al. | |

(56) References Cited

U.S. PATENT DOCUMENTS

| | | |
|---|---|---|
| 5,581,638 A | 12/1996 | Givens et al. |
| 5,586,054 A | 12/1996 | Jensen et al. |
| 5,592,939 A | 1/1997 | Martinelli |
| 5,596,079 A | 1/1997 | Smith et al. |
| 5,598,844 A | 2/1997 | Diaz et al. |
| 5,609,606 A | 3/1997 | O'Boyle |
| 5,630,806 A | 5/1997 | Inagaki et al. |
| 5,651,366 A | 7/1997 | Liang et al. |
| 5,660,180 A | 8/1997 | Malinowski et al. |
| 5,667,499 A | 9/1997 | Welch et al. |
| 5,667,521 A | 9/1997 | Keown |
| 5,672,877 A | 9/1997 | Liebig et al. |
| 5,674,232 A | 10/1997 | Halliburton |
| 5,693,015 A | 12/1997 | Walker et al. |
| 5,713,848 A | 2/1998 | Dubrul et al. |
| 5,745,634 A | 4/1998 | Garrett et al. |
| 5,771,895 A | 6/1998 | Slager |
| 5,779,642 A | 7/1998 | Nightengale |
| 5,779,731 A | 7/1998 | Leavitt |
| 5,780,958 A | 7/1998 | Strugach et al. |
| 5,798,521 A | 8/1998 | Froggatt |
| 5,800,450 A | 9/1998 | Lary et al. |
| 5,803,083 A | 9/1998 | Buck et al. |
| 5,814,061 A | 9/1998 | Osborne et al. |
| 5,817,025 A | 10/1998 | Alekseev et al. |
| 5,820,594 A | 10/1998 | Fontirroche et al. |
| 5,824,520 A | 10/1998 | Mulligan-Kehoe |
| 5,827,313 A | 10/1998 | Ream |
| 5,830,222 A | 11/1998 | Makower |
| 5,848,121 A | 12/1998 | Gupta et al. |
| 5,851,464 A | 12/1998 | Davila et al. |
| 5,857,974 A | 1/1999 | Eberle et al. |
| 5,872,829 A | 2/1999 | Wischmann et al. |
| 5,873,835 A | 2/1999 | Hastings et al. |
| 5,882,722 A | 3/1999 | Kydd |
| 5,912,764 A | 6/1999 | Togino |
| 5,916,194 A | 6/1999 | Jacobsen et al. |
| 5,921,931 A | 7/1999 | O'Donnell et al. |
| 5,925,055 A | 7/1999 | Adrian et al. |
| 5,949,929 A | 9/1999 | Hamm |
| 5,951,586 A | 9/1999 | Berg et al. |
| 5,974,521 A | 10/1999 | Akerib |
| 5,976,120 A | 11/1999 | Chow et al. |
| 5,978,391 A | 11/1999 | Das et al. |
| 5,997,523 A | 12/1999 | Jang |
| 6,021,240 A | 2/2000 | Murphy et al. |
| 6,022,319 A | 2/2000 | Willard et al. |
| 6,031,071 A | 2/2000 | Mandeville et al. |
| 6,036,889 A | 3/2000 | Kydd |
| 6,043,883 A | 3/2000 | Leckel et al. |
| 6,050,949 A | 4/2000 | White et al. |
| 6,059,738 A | 5/2000 | Stoltze et al. |
| 6,068,638 A | 5/2000 | Makower |
| 6,074,362 A | 6/2000 | Jang et al. |
| 6,078,831 A | 6/2000 | Belef et al. |
| 6,080,109 A | 6/2000 | Baker et al. |
| 6,091,496 A | 7/2000 | Hill |
| 6,094,591 A | 7/2000 | Foltz et al. |
| 6,095,976 A | 8/2000 | Nachtomy et al. |
| 6,097,755 A | 8/2000 | Guenther, Jr. et al. |
| 6,099,471 A | 8/2000 | Torp et al. |
| 6,099,549 A | 8/2000 | Bosma et al. |
| 6,102,938 A | 8/2000 | Evans et al. |
| 6,106,476 A | 8/2000 | Corl et al. |
| 6,120,445 A | 9/2000 | Grunwald |
| 6,123,673 A | 9/2000 | Eberle et al. |
| 6,134,003 A | 10/2000 | Tearney et al. |
| 6,139,510 A | 10/2000 | Palermo |
| 6,141,089 A | 10/2000 | Thoma et al. |
| 6,146,328 A | 11/2000 | Chiao et al. |
| 6,148,095 A | 11/2000 | Prause et al. |
| 6,151,433 A | 11/2000 | Dower et al. |
| 6,152,877 A | 11/2000 | Masters |
| 6,152,878 A | 11/2000 | Nachtomy et al. |
| 6,159,225 A | 12/2000 | Makower |
| 6,165,127 A | 12/2000 | Crowley |
| 6,176,842 B1 | 1/2001 | Tachibana et al. |
| 6,179,809 B1 | 1/2001 | Khairkhahan et al. |
| 6,186,949 B1 | 2/2001 | Hatfield et al. |
| 6,190,353 B1 | 2/2001 | Makower et al. |
| 6,200,266 B1 | 3/2001 | Shokrollahi et al. |
| 6,200,268 B1 | 3/2001 | Vince et al. |
| 6,203,537 B1 | 3/2001 | Adrian |
| 6,208,415 B1 | 3/2001 | De Boer et al. |
| 6,210,332 B1 | 4/2001 | Chiao et al. |
| 6,210,339 B1 | 4/2001 | Kiepen et al. |
| 6,212,308 B1 | 4/2001 | Donald |
| 6,231,518 B1 | 5/2001 | Grabek et al. |
| 6,245,066 B1 | 6/2001 | Morgan et al. |
| 6,249,076 B1 | 6/2001 | Madden et al. |
| 6,254,543 B1 | 7/2001 | Grunwald et al. |
| 6,256,090 B1 | 7/2001 | Chen et al. |
| 6,258,052 B1 | 7/2001 | Milo |
| 6,261,246 B1 | 7/2001 | Pantages et al. |
| 6,275,628 B1 | 8/2001 | Jones et al. |
| 6,283,921 B1 | 9/2001 | Nix et al. |
| 6,283,951 B1 | 9/2001 | Flaherty et al. |
| 6,295,308 B1 | 9/2001 | Zah |
| 6,299,622 B1 | 10/2001 | Snow et al. |
| 6,312,384 B1 | 11/2001 | Chiao |
| 6,325,797 B1 | 12/2001 | Stewart et al. |
| 6,328,696 B1 | 12/2001 | Fraser |
| 6,343,168 B1 | 1/2002 | Murphy et al. |
| 6,343,178 B1 | 1/2002 | Burns et al. |
| 6,350,240 B1 | 2/2002 | Song et al. |
| 6,364,841 B1 | 4/2002 | White et al. |
| 6,366,722 B1 | 4/2002 | Murphy et al. |
| 6,367,984 B1 | 4/2002 | Stephenson et al. |
| 6,373,970 B1 | 4/2002 | Dong et al. |
| 6,375,615 B1 | 4/2002 | Flaherty et al. |
| 6,375,618 B1 | 4/2002 | Chiao et al. |
| 6,375,628 B1 | 4/2002 | Zadno-Azizi et al. |
| 6,376,830 B1 | 4/2002 | Froggatt et al. |
| 6,379,352 B1 | 4/2002 | Reynolds et al. |
| 6,381,350 B1 | 4/2002 | Klingensmith et al. |
| 6,387,124 B1 | 5/2002 | Buscemi et al. |
| 6,396,976 B1 | 5/2002 | Little et al. |
| 6,398,792 B1 | 6/2002 | O'Connor |
| 6,417,948 B1 | 7/2002 | Chowdhury et al. |
| 6,419,644 B1 | 7/2002 | White et al. |
| 6,421,164 B2 | 7/2002 | Tearney et al. |
| 6,423,012 B1 | 7/2002 | Kato et al. |
| 6,426,796 B1 | 7/2002 | Pulliam et al. |
| 6,428,041 B1 | 8/2002 | Wohllebe et al. |
| 6,428,498 B2 | 8/2002 | Uflacker |
| 6,429,421 B1 | 8/2002 | Meller et al. |
| 6,440,077 B1 | 8/2002 | Jung et al. |
| 6,443,903 B1 | 9/2002 | White et al. |
| 6,450,964 B1 | 9/2002 | Webler |
| 6,457,365 B1 | 10/2002 | Stephens et al. |
| 6,459,844 B1 | 10/2002 | Pan |
| 6,468,290 B1 | 10/2002 | Weldon et al. |
| 6,475,149 B1 | 11/2002 | Sumanaweera |
| 6,480,285 B1 | 11/2002 | Hill |
| 6,491,631 B2 | 12/2002 | Chiao et al. |
| 6,491,636 B2 | 12/2002 | Chenal et al. |
| 6,501,551 B1 | 12/2002 | Tearney et al. |
| 6,504,286 B1 | 1/2003 | Porat et al. |
| 6,508,824 B1 | 1/2003 | Flaherty et al. |
| 6,514,237 B1 | 2/2003 | Maseda |
| 6,520,269 B2 | 2/2003 | Geiger et al. |
| 6,520,677 B2 | 2/2003 | Iizuka |
| 6,535,764 B2 | 3/2003 | Imran et al. |
| 6,538,778 B1 | 3/2003 | Leckel et al. |
| 6,544,217 B1 | 4/2003 | Gulachenski |
| 6,544,230 B1 | 4/2003 | Flaherty et al. |
| 6,545,760 B1 | 4/2003 | Froggatt et al. |
| 6,546,272 B1 | 4/2003 | MacKinnon et al. |
| 6,551,250 B2 | 4/2003 | Khalil |
| 6,566,648 B1 | 5/2003 | Froggatt |
| 6,570,894 B2 | 5/2003 | Anderson |
| 6,572,555 B2 | 6/2003 | White et al. |
| 6,579,311 B1 | 6/2003 | Makower |
| 6,584,335 B1 | 6/2003 | Haar et al. |

(56) References Cited

U.S. PATENT DOCUMENTS

| | | | |
|---|---|---|---|
| 6,592,612 | B1 | 7/2003 | Samson et al. |
| 6,594,448 | B2 | 7/2003 | Herman et al. |
| 6,602,241 | B2 | 8/2003 | Makower et al. |
| 6,611,322 | B1 | 8/2003 | Nakayama et al. |
| 6,611,720 | B2 | 8/2003 | Hata et al. |
| 6,612,992 | B1 | 9/2003 | Hossack et al. |
| 6,615,062 | B2 | 9/2003 | Ryan et al. |
| 6,615,072 | B1 | 9/2003 | Izatt et al. |
| 6,621,562 | B2 | 9/2003 | Durston |
| 6,631,284 | B2 | 10/2003 | Nutt et al. |
| 6,638,227 | B2 | 10/2003 | Bae |
| 6,645,152 | B1 | 11/2003 | Jung et al. |
| 6,646,745 | B2 | 11/2003 | Verma et al. |
| 6,655,386 | B1 | 12/2003 | Makower et al. |
| 6,659,957 | B1 | 12/2003 | Vardi et al. |
| 6,660,024 | B1 | 12/2003 | Flaherty et al. |
| 6,663,565 | B2 | 12/2003 | Kawagishi et al. |
| 6,665,456 | B2 | 12/2003 | Dave et al. |
| 6,669,716 | B1 | 12/2003 | Gilson et al. |
| 6,671,055 | B1 | 12/2003 | Wavering et al. |
| 6,673,015 | B1 | 1/2004 | Glover et al. |
| 6,673,064 | B1 | 1/2004 | Rentrop |
| 6,685,648 | B2 | 2/2004 | Flaherty et al. |
| 6,689,056 | B1 | 2/2004 | Kilcoyne et al. |
| 6,689,144 | B2 | 2/2004 | Gerberding |
| 6,696,173 | B1 | 2/2004 | Naundorf et al. |
| 6,701,044 | B2 | 3/2004 | Arbore et al. |
| 6,701,176 | B1 | 3/2004 | Halperin et al. |
| 6,709,444 | B1 | 3/2004 | Makower |
| 6,712,836 | B1 | 3/2004 | Berg et al. |
| 6,714,703 | B2 | 3/2004 | Lee et al. |
| 6,719,717 | B1 | 4/2004 | Johnson et al. |
| 6,725,073 | B1 | 4/2004 | Motamedi et al. |
| 6,726,677 | B1 | 4/2004 | Flaherty et al. |
| 6,730,107 | B2 | 5/2004 | Kelley et al. |
| 6,733,474 | B2 | 5/2004 | Kusleika |
| 6,738,144 | B1 | 5/2004 | Dogariu |
| 6,740,113 | B2 | 5/2004 | Vrba |
| 6,746,464 | B1 | 6/2004 | Makower |
| 6,780,157 | B2 | 8/2004 | Stephens et al. |
| 6,795,188 | B2 | 9/2004 | Ruck et al. |
| 6,795,196 | B2 | 9/2004 | Funakawa |
| 6,798,522 | B2 | 9/2004 | Stolte et al. |
| 6,822,798 | B2 | 11/2004 | Wu et al. |
| 6,830,559 | B2 | 12/2004 | Schock |
| 6,832,024 | B2 | 12/2004 | Gerstenberger et al. |
| 6,842,639 | B1 | 1/2005 | Winston et al. |
| 6,847,449 | B2 | 1/2005 | Bashkansky et al. |
| 6,855,115 | B2 | 2/2005 | Fonseca et al. |
| 6,856,138 | B2 | 2/2005 | Bohley |
| 6,856,400 | B1 | 2/2005 | Froggatt |
| 6,856,472 | B2 | 2/2005 | Herman et al. |
| 6,860,867 | B2 | 3/2005 | Seward et al. |
| 6,866,670 | B2 | 3/2005 | Rabiner et al. |
| 6,878,113 | B2 | 4/2005 | Miwa et al. |
| 6,886,411 | B2 | 5/2005 | Kjellman et al. |
| 6,891,984 | B2 | 5/2005 | Petersen et al. |
| 6,895,106 | B2 | 5/2005 | Wang et al. |
| 6,898,337 | B2 | 5/2005 | Averett et al. |
| 6,900,897 | B2 | 5/2005 | Froggatt |
| 6,912,051 | B2 | 6/2005 | Jensen |
| 6,916,329 | B1 | 7/2005 | Zhao |
| 6,922,498 | B2 | 7/2005 | Shah |
| 6,937,346 | B2 | 8/2005 | Nebendahl et al. |
| 6,937,696 | B1 | 8/2005 | Mostafavi |
| 6,943,939 | B1 | 9/2005 | DiJaili et al. |
| 6,947,147 | B2 | 9/2005 | Motamedi et al. |
| 6,947,787 | B2 | 9/2005 | Webler |
| 6,949,094 | B2 | 9/2005 | Yaron |
| 6,952,603 | B2 | 10/2005 | Gerber et al. |
| 6,954,737 | B2 | 10/2005 | Kalantar et al. |
| 6,958,042 | B2 | 10/2005 | Honda |
| 6,961,123 | B1 | 11/2005 | Wang et al. |
| 6,966,891 | B2 | 11/2005 | Ookubo et al. |
| 6,969,293 | B2 | 11/2005 | Thai |
| 6,969,395 | B2 | 11/2005 | Eskuri |
| 6,985,234 | B2 | 1/2006 | Anderson |
| 7,004,963 | B2 | 2/2006 | Wang et al. |
| 7,006,231 | B2 | 2/2006 | Ostrovsky et al. |
| 7,010,458 | B2 | 3/2006 | Wilt |
| 7,024,025 | B2 | 4/2006 | Sathyanarayana |
| 7,027,211 | B1 | 4/2006 | Ruffa |
| 7,027,743 | B1 | 4/2006 | Tucker et al. |
| 7,033,347 | B2 | 4/2006 | Appling |
| 7,035,484 | B2 | 4/2006 | Silberberg et al. |
| 7,037,269 | B2 | 5/2006 | Nix et al. |
| 7,042,573 | B2 | 5/2006 | Froggatt |
| 7,044,915 | B2 | 5/2006 | White et al. |
| 7,044,964 | B2 | 5/2006 | Jang et al. |
| 7,048,711 | B2 | 5/2006 | Rosenman et al. |
| 7,049,306 | B2 | 5/2006 | Konradi et al. |
| 7,058,239 | B2 | 6/2006 | Singh et al. |
| 7,060,033 | B2 | 6/2006 | White et al. |
| 7,060,421 | B2 | 6/2006 | Naundorf et al. |
| 7,063,679 | B2 | 6/2006 | Maguire et al. |
| 7,068,852 | B2 | 6/2006 | Braica |
| 7,074,188 | B2 | 7/2006 | Nair et al. |
| 7,095,493 | B2 | 8/2006 | Harres |
| 7,110,119 | B2 | 9/2006 | Maestle |
| 7,113,875 | B2 | 9/2006 | Terashima et al. |
| 7,123,777 | B2 | 10/2006 | Rondinelli et al. |
| 7,130,054 | B2 | 10/2006 | Ostrovsky et al. |
| 7,139,440 | B2 | 11/2006 | Rondinelli et al. |
| 7,153,299 | B1 | 12/2006 | Tu et al. |
| 7,171,078 | B2 | 1/2007 | Sasaki et al. |
| 7,175,597 | B2 | 2/2007 | Vince et al. |
| 7,177,491 | B2 | 2/2007 | Dave et al. |
| 7,190,464 | B2 | 3/2007 | Alphonse |
| 7,215,802 | B2 | 5/2007 | Klingensmith et al. |
| 7,218,811 | B2 | 5/2007 | Shigenaga et al. |
| 7,236,812 | B1 | 6/2007 | Ballerstadt et al. |
| 7,245,125 | B2 | 7/2007 | Harer et al. |
| 7,245,789 | B2 | 7/2007 | Bates et al. |
| 7,249,357 | B2 | 7/2007 | Landman et al. |
| 7,291,146 | B2 | 11/2007 | Steinke et al. |
| 7,292,715 | B2 | 11/2007 | Furnish |
| 7,292,885 | B2 | 11/2007 | Scott et al. |
| 7,294,124 | B2 | 11/2007 | Eidenschink |
| 7,300,460 | B2 | 11/2007 | Levine et al. |
| 7,335,161 | B2 | 2/2008 | Von Arx et al. |
| 7,337,079 | B2 | 2/2008 | Park et al. |
| 7,355,716 | B2 | 4/2008 | de Boer et al. |
| 7,356,367 | B2 | 4/2008 | Liang et al. |
| 7,358,921 | B2 | 4/2008 | Snyder et al. |
| 7,359,062 | B2 | 4/2008 | Chen et al. |
| 7,359,554 | B2 | 4/2008 | Klingensmith et al. |
| 7,363,927 | B2 | 4/2008 | Ravikumar |
| 7,366,376 | B2 | 4/2008 | Shishkov et al. |
| 7,382,949 | B2 | 6/2008 | Bouma et al. |
| 7,387,636 | B2 | 6/2008 | Cohn et al. |
| 7,391,520 | B2 | 6/2008 | Zhou et al. |
| 7,397,935 | B2 | 7/2008 | Kimmel et al. |
| 7,399,095 | B2 | 7/2008 | Rondinelli |
| 7,408,648 | B2 | 8/2008 | Kleen et al. |
| 7,414,779 | B2 | 8/2008 | Huber et al. |
| 7,440,087 | B2 | 10/2008 | Froggatt et al. |
| 7,447,388 | B2 | 11/2008 | Bates et al. |
| 7,449,821 | B2 | 11/2008 | Dausch |
| 7,450,165 | B2 | 11/2008 | Ahiska |
| RE40,608 | E | 12/2008 | Glover et al. |
| 7,458,967 | B2 | 12/2008 | Appling et al. |
| 7,463,362 | B2 | 12/2008 | Lasker et al. |
| 7,463,759 | B2 | 12/2008 | Klingensmith et al. |
| 7,491,226 | B2 | 2/2009 | Palmaz et al. |
| 7,515,276 | B2 | 4/2009 | Froggatt et al. |
| 7,527,594 | B2 | 5/2009 | Vardi et al. |
| 7,534,251 | B2 | 5/2009 | WasDyke |
| 7,535,797 | B2 | 5/2009 | Peng et al. |
| 7,547,304 | B2 | 6/2009 | Johnson |
| 7,564,949 | B2 | 7/2009 | Sattler et al. |
| 7,577,471 | B2 | 8/2009 | Camus et al. |
| 7,583,857 | B2 | 9/2009 | Xu et al. |
| 7,603,165 | B2 | 10/2009 | Townsend et al. |
| 7,612,773 | B2 | 11/2009 | Magnin et al. |

(56) References Cited

U.S. PATENT DOCUMENTS

| | | |
|---|---|---|
| 7,633,627 B2 | 12/2009 | Choma et al. |
| 7,645,229 B2 | 1/2010 | Armstrong |
| 7,658,715 B2 | 2/2010 | Park et al. |
| 7,660,452 B2 | 2/2010 | Zwirn et al. |
| 7,660,492 B2 | 2/2010 | Bates et al. |
| 7,666,204 B2 | 2/2010 | Thornton et al. |
| 7,672,790 B2 | 3/2010 | McGraw et al. |
| 7,680,247 B2 | 3/2010 | Atzinger et al. |
| 7,684,991 B2 | 3/2010 | Stohr et al. |
| 7,711,413 B2 | 5/2010 | Feldman et al. |
| 7,720,322 B2 | 5/2010 | Prisco |
| 7,728,986 B2 | 6/2010 | Lasker et al. |
| 7,734,009 B2 | 6/2010 | Brunner et al. |
| 7,736,317 B2 | 6/2010 | Stephens et al. |
| 7,742,795 B2 | 6/2010 | Stone et al. |
| 7,743,189 B2 | 6/2010 | Brown et al. |
| 7,762,954 B2 | 7/2010 | Nix et al. |
| 7,766,896 B2 | 8/2010 | Kornkven Volk et al. |
| 7,773,792 B2 | 8/2010 | Kimmel et al. |
| 7,775,981 B1 | 8/2010 | Guracar et al. |
| 7,777,399 B2 | 8/2010 | Eidenschink et al. |
| 7,781,724 B2 | 8/2010 | Childers et al. |
| 7,783,337 B2 | 8/2010 | Feldman et al. |
| 7,787,127 B2 | 8/2010 | Galle et al. |
| 7,792,342 B2 | 9/2010 | Barbu et al. |
| 7,801,343 B2 | 9/2010 | Unal et al. |
| 7,801,590 B2 | 9/2010 | Feldman et al. |
| 7,813,609 B2 | 10/2010 | Petersen et al. |
| 7,831,081 B2 | 11/2010 | Li |
| 7,846,101 B2 | 12/2010 | Eberle et al. |
| 7,853,104 B2 | 12/2010 | Oota et al. |
| 7,853,316 B2 | 12/2010 | Milner et al. |
| 7,860,555 B2 | 12/2010 | Saadat |
| 7,862,508 B2 | 1/2011 | Davies et al. |
| 7,872,759 B2 | 1/2011 | Tearney et al. |
| 7,880,868 B2 | 2/2011 | Aoki |
| 7,881,763 B2 | 2/2011 | Brauker et al. |
| 7,909,844 B2 | 3/2011 | Alkhatib et al. |
| 7,921,854 B2 | 4/2011 | Hennings et al. |
| 7,927,784 B2 | 4/2011 | Simpson |
| 7,929,148 B2 | 4/2011 | Kemp |
| 7,930,014 B2 | 4/2011 | Huennekens et al. |
| 7,930,104 B2 | 4/2011 | Baker et al. |
| 7,936,462 B2 | 5/2011 | Jiang et al. |
| 7,942,852 B2 | 5/2011 | Mas et al. |
| 7,947,012 B2 | 5/2011 | Spurchise et al. |
| 7,951,186 B2 | 5/2011 | Eidenschink et al. |
| 7,952,719 B2 | 5/2011 | Brennan, III |
| 7,972,353 B2 | 7/2011 | Hendriksen et al. |
| 7,976,492 B2 | 7/2011 | Brauker et al. |
| 7,977,950 B2 | 7/2011 | Maslen |
| 7,978,916 B2 | 7/2011 | Klingensmith et al. |
| 7,981,041 B2 | 7/2011 | McGahan |
| 7,981,151 B2 | 7/2011 | Rowe |
| 7,983,737 B2 | 7/2011 | Feldman et al. |
| 7,993,333 B2 | 8/2011 | Oral et al. |
| 7,995,210 B2 | 8/2011 | Tearney et al. |
| 7,996,060 B2 | 8/2011 | Trofimov et al. |
| 7,999,938 B2 | 8/2011 | Wang |
| 8,021,377 B2 | 9/2011 | Eskuri |
| 8,021,420 B2 | 9/2011 | Dolan |
| 8,036,732 B2 | 10/2011 | Milner |
| 8,040,586 B2 | 10/2011 | Smith et al. |
| 8,047,996 B2 | 11/2011 | Goodnow et al. |
| 8,049,900 B2 | 11/2011 | Kemp et al. |
| 8,050,478 B2 | 11/2011 | Li et al. |
| 8,050,523 B2 | 11/2011 | Younge et al. |
| 8,052,605 B2 | 11/2011 | Muller et al. |
| 8,057,394 B2 | 11/2011 | Dala-Krishna |
| 8,059,923 B2 | 11/2011 | Bates et al. |
| 8,070,800 B2 | 12/2011 | Lock et al. |
| 8,080,800 B2 | 12/2011 | Hoctor et al. |
| 8,088,102 B2 | 1/2012 | Adams et al. |
| 8,100,838 B2 | 1/2012 | Wright et al. |
| 8,104,479 B2 | 1/2012 | Glynn et al. |
| 8,108,030 B2 | 1/2012 | Castella et al. |
| 8,114,102 B2 | 2/2012 | Galdonik et al. |
| 8,116,605 B2 | 2/2012 | Petersen et al. |
| 8,125,648 B2 | 2/2012 | Milner et al. |
| 8,126,239 B2 | 2/2012 | Sun et al. |
| 8,133,199 B2 | 3/2012 | Weber et al. |
| 8,133,269 B2 | 3/2012 | Flechsenhar et al. |
| 8,140,708 B2 | 3/2012 | Zaharia et al. |
| 8,148,877 B2 | 4/2012 | Jiang et al. |
| 8,167,932 B2 | 5/2012 | Bourang et al. |
| 8,172,757 B2 | 5/2012 | Jaffe et al. |
| 8,177,809 B2 | 5/2012 | Mavani et al. |
| 8,187,191 B2 | 5/2012 | Hancock et al. |
| 8,187,267 B2 | 5/2012 | Pappone et al. |
| 8,187,830 B2 | 5/2012 | Hu et al. |
| 8,199,218 B2 | 6/2012 | Lee et al. |
| 8,206,429 B2 | 6/2012 | Gregorich et al. |
| 8,208,995 B2 | 6/2012 | Tearney et al. |
| 8,222,906 B2 | 7/2012 | Wyar et al. |
| 8,233,681 B2 | 7/2012 | Aylward et al. |
| 8,233,718 B2 | 7/2012 | Klingensmith et al. |
| 8,238,624 B2 | 8/2012 | Doi et al. |
| 8,239,938 B2 | 8/2012 | Simeral et al. |
| 8,277,386 B2 | 10/2012 | Ahmed et al. |
| 8,280,470 B2 | 10/2012 | Milner et al. |
| 8,289,284 B2 | 10/2012 | Glynn et al. |
| 8,289,522 B2 | 10/2012 | Tearney et al. |
| 8,298,147 B2 | 10/2012 | Huennekens et al. |
| 8,298,149 B2 | 10/2012 | Hastings et al. |
| 8,301,000 B2 | 10/2012 | Sillard et al. |
| 8,309,428 B2 | 11/2012 | Lemmerhirt et al. |
| 8,317,713 B2 | 11/2012 | Davies et al. |
| 8,323,201 B2 | 12/2012 | Towfiq et al. |
| 8,329,053 B2 | 12/2012 | Martin et al. |
| 8,336,643 B2 | 12/2012 | Harleman |
| 8,349,000 B2 | 1/2013 | Schreck |
| 8,353,945 B2 | 1/2013 | Andreas et al. |
| 8,353,954 B2 | 1/2013 | Cai et al. |
| 8,357,981 B2 | 1/2013 | Martin et al. |
| 8,361,097 B2 | 1/2013 | Patel et al. |
| 8,386,560 B2 | 2/2013 | Ma et al. |
| 8,398,591 B2 | 3/2013 | Mas et al. |
| 8,412,312 B2 | 4/2013 | Judell et al. |
| 8,417,491 B2 | 4/2013 | Trovato et al. |
| 8,449,465 B2 | 5/2013 | Nair et al. |
| 8,454,685 B2 | 6/2013 | Hariton et al. |
| 8,454,686 B2 | 6/2013 | Alkhatib |
| 8,475,522 B2 | 7/2013 | Jimenez et al. |
| 8,478,384 B2 | 7/2013 | Schmitt et al. |
| 8,486,062 B2 | 7/2013 | Belhe et al. |
| 8,486,063 B2 | 7/2013 | Werneth et al. |
| 8,491,567 B2 | 7/2013 | Magnin et al. |
| 8,500,798 B2 | 8/2013 | Rowe et al. |
| 8,550,911 B2 | 10/2013 | Sylla |
| 8,594,757 B2 | 11/2013 | Boppart et al. |
| 8,597,349 B2 | 12/2013 | Alkhatib |
| 8,600,477 B2 | 12/2013 | Beyar et al. |
| 8,600,917 B1 | 12/2013 | Schimert et al. |
| 8,601,056 B2 | 12/2013 | Lauwers et al. |
| 8,620,055 B2 | 12/2013 | Barratt et al. |
| 8,644,910 B2 | 2/2014 | Rousso et al. |
| 2001/0007940 A1 | 7/2001 | Tu et al. |
| 2001/0029337 A1 | 10/2001 | Pantages et al. |
| 2001/0037073 A1 | 11/2001 | White et al. |
| 2001/0046345 A1 | 11/2001 | Snyder et al. |
| 2001/0049548 A1 | 12/2001 | Vardi et al. |
| 2002/0034276 A1 | 3/2002 | Hu et al. |
| 2002/0041723 A1 | 4/2002 | Ronnekleiv et al. |
| 2002/0069676 A1 | 6/2002 | Kopp, II et al. |
| 2002/0089335 A1 | 7/2002 | Williams |
| 2002/0099289 A1 | 7/2002 | Crowley |
| 2002/0163646 A1 | 11/2002 | Anderson |
| 2002/0186818 A1 | 12/2002 | Arnaud et al. |
| 2002/0196446 A1 | 12/2002 | Roth et al. |
| 2002/0197456 A1 | 12/2002 | Pope |
| 2003/0004412 A1 | 1/2003 | Izatt et al. |
| 2003/0016604 A1 | 1/2003 | Hanes |
| 2003/0018273 A1 | 1/2003 | Corl et al. |
| 2003/0023153 A1 | 1/2003 | Izatt et al. |

(56) References Cited

U.S. PATENT DOCUMENTS

| | | |
|---|---|---|
| 2003/0032886 A1 | 2/2003 | Dgany et al. |
| 2003/0050871 A1 | 3/2003 | Broughton |
| 2003/0060716 A1 | 3/2003 | Heidrich |
| 2003/0065371 A1 | 4/2003 | Satake |
| 2003/0069723 A1 | 4/2003 | Hegde |
| 2003/0077043 A1 | 4/2003 | Hamm et al. |
| 2003/0085635 A1 | 5/2003 | Davidsen |
| 2003/0090753 A1 | 5/2003 | Takeyama et al. |
| 2003/0092995 A1 | 5/2003 | Thompson |
| 2003/0093059 A1 | 5/2003 | Griffin et al. |
| 2003/0103212 A1 | 6/2003 | Westphal et al. |
| 2003/0152259 A1 | 8/2003 | Belykh et al. |
| 2003/0181802 A1 | 9/2003 | Ogawa |
| 2003/0187369 A1 | 10/2003 | Lewis et al. |
| 2003/0194165 A1 | 10/2003 | Silberberg et al. |
| 2003/0195419 A1 | 10/2003 | Harada |
| 2003/0208116 A1 | 11/2003 | Liang et al. |
| 2003/0212491 A1 | 11/2003 | Mitchell et al. |
| 2003/0219202 A1 | 11/2003 | Loeb et al. |
| 2003/0220749 A1 | 11/2003 | Chen et al. |
| 2003/0228039 A1 | 12/2003 | Green |
| 2004/0015065 A1 | 1/2004 | Panescu et al. |
| 2004/0023317 A1 | 2/2004 | Motamedi et al. |
| 2004/0028333 A1 | 2/2004 | Lomas |
| 2004/0037742 A1 | 2/2004 | Jen et al. |
| 2004/0042066 A1 | 3/2004 | Kinoshita et al. |
| 2004/0054287 A1 | 3/2004 | Stephens |
| 2004/0067000 A1 | 4/2004 | Bates et al. |
| 2004/0068161 A1 | 4/2004 | Couvillon |
| 2004/0082844 A1 | 4/2004 | Vardi et al. |
| 2004/0092830 A1 | 5/2004 | Scott et al. |
| 2004/0106853 A1 | 6/2004 | Moriyama |
| 2004/0111552 A1 | 6/2004 | Arimilli et al. |
| 2004/0126048 A1 | 7/2004 | Dave et al. |
| 2004/0143160 A1 | 7/2004 | Couvillon |
| 2004/0146546 A1 | 7/2004 | Gravett et al. |
| 2004/0186369 A1 | 9/2004 | Lam |
| 2004/0186558 A1 | 9/2004 | Pavcnik et al. |
| 2004/0195512 A1 | 10/2004 | Crosetto |
| 2004/0220606 A1 | 11/2004 | Goshgarian |
| 2004/0225220 A1 | 11/2004 | Rich |
| 2004/0239938 A1 | 12/2004 | Izatt |
| 2004/0242990 A1 | 12/2004 | Brister et al. |
| 2004/0248439 A1 | 12/2004 | Gernhardt et al. |
| 2004/0260236 A1 | 12/2004 | Manning et al. |
| 2005/0013778 A1 | 1/2005 | Green et al. |
| 2005/0031176 A1 | 2/2005 | Hertel et al. |
| 2005/0036150 A1 | 2/2005 | Izatt et al. |
| 2005/0078317 A1 | 4/2005 | Law et al. |
| 2005/0101859 A1 | 5/2005 | Maschke |
| 2005/0140582 A1 | 6/2005 | Lee et al. |
| 2005/0140682 A1 | 6/2005 | Sumanaweera et al. |
| 2005/0140981 A1 | 6/2005 | Waelti |
| 2005/0140984 A1 | 6/2005 | Hitzenberger |
| 2005/0147303 A1 | 7/2005 | Zhou et al. |
| 2005/0165439 A1 | 7/2005 | Weber et al. |
| 2005/0171433 A1 | 8/2005 | Boppart et al. |
| 2005/0171438 A1 | 8/2005 | Chen et al. |
| 2005/0182297 A1 | 8/2005 | Gravenstein et al. |
| 2005/0196028 A1 | 9/2005 | Kleen et al. |
| 2005/0197585 A1 | 9/2005 | Brockway et al. |
| 2005/0213103 A1 | 9/2005 | Everett et al. |
| 2005/0215942 A1 | 9/2005 | Abrahamson et al. |
| 2005/0234445 A1 | 10/2005 | Conquergood et al. |
| 2005/0243322 A1 | 11/2005 | Lasker et al. |
| 2005/0249391 A1 | 11/2005 | Kimmel et al. |
| 2005/0251567 A1 | 11/2005 | Bellew et al. |
| 2005/0254059 A1 | 11/2005 | Alphonse |
| 2005/0264823 A1 | 12/2005 | Zhu et al. |
| 2006/0013523 A1 | 1/2006 | Childers et al. |
| 2006/0015126 A1 | 1/2006 | Sher |
| 2006/0029634 A1 | 2/2006 | Berg et al. |
| 2006/0036167 A1 | 2/2006 | Shina |
| 2006/0038115 A1 | 2/2006 | Maas |
| 2006/0039004 A1 | 2/2006 | de Boer et al. |
| 2006/0041180 A1 | 2/2006 | Viswanathan et al. |
| 2006/0045536 A1 | 3/2006 | Arahira |
| 2006/0055936 A1 | 3/2006 | Yun et al. |
| 2006/0058622 A1 | 3/2006 | Tearney et al. |
| 2006/0064009 A1 | 3/2006 | Webler et al. |
| 2006/0067620 A1 | 3/2006 | Shishkov et al. |
| 2006/0072808 A1 | 4/2006 | Grimm et al. |
| 2006/0074442 A1 | 4/2006 | Noriega et al. |
| 2006/0098927 A1 | 5/2006 | Schmidt et al. |
| 2006/0100694 A1 | 5/2006 | Globerman |
| 2006/0106375 A1 | 5/2006 | Werneth et al. |
| 2006/0132790 A1 | 6/2006 | Gutin |
| 2006/0135870 A1 | 6/2006 | Webler |
| 2006/0142703 A1 | 6/2006 | Carter et al. |
| 2006/0142733 A1 | 6/2006 | Forsberg |
| 2006/0173299 A1 | 8/2006 | Romley et al. |
| 2006/0179255 A1 | 8/2006 | Yamazaki |
| 2006/0184048 A1 | 8/2006 | Saadat |
| 2006/0187537 A1 | 8/2006 | Huber et al. |
| 2006/0195269 A1 | 8/2006 | Yeatman et al. |
| 2006/0204119 A1 | 9/2006 | Feng et al. |
| 2006/0229591 A1 | 10/2006 | Lee |
| 2006/0239312 A1 | 10/2006 | Kewitsch et al. |
| 2006/0241342 A1 | 10/2006 | Macaulay et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2006/0258895 A1 | 11/2006 | Maschke |
| 2006/0264743 A1 | 11/2006 | Kleen et al. |
| 2006/0267756 A1 | 11/2006 | Kates |
| 2006/0270976 A1 | 11/2006 | Savage et al. |
| 2006/0276709 A1 | 12/2006 | Khamene et al. |
| 2006/0279742 A1 | 12/2006 | Tearney et al. |
| 2006/0279743 A1 | 12/2006 | Boesser et al. |
| 2006/0285638 A1 | 12/2006 | Boese et al. |
| 2006/0287595 A1 | 12/2006 | Maschke |
| 2006/0293597 A1 | 12/2006 | Johnson et al. |
| 2007/0015969 A1 | 1/2007 | Feldman et al. |
| 2007/0016029 A1 | 1/2007 | Donaldson et al. |
| 2007/0016030 A1* | 1/2007 | Stringer .............. A61B 8/0833 600/437 |
| 2007/0016034 A1 | 1/2007 | Donaldson |
| 2007/0016062 A1 | 1/2007 | Park et al. |
| 2007/0027390 A1 | 2/2007 | Maschke et al. |
| 2007/0036417 A1 | 2/2007 | Argiro et al. |
| 2007/0038061 A1 | 2/2007 | Huennekens et al. |
| 2007/0038121 A1 | 2/2007 | Feldman et al. |
| 2007/0038125 A1 | 2/2007 | Kleen et al. |
| 2007/0043292 A1 | 2/2007 | Camus et al. |
| 2007/0043597 A1 | 2/2007 | Donaldson |
| 2007/0049847 A1 | 3/2007 | Osborne |
| 2007/0060973 A1 | 3/2007 | Ludvig et al. |
| 2007/0065077 A1 | 3/2007 | Childers et al. |
| 2007/0066888 A1 | 3/2007 | Maschke |
| 2007/0066890 A1 | 3/2007 | Maschke |
| 2007/0066983 A1 | 3/2007 | Maschke |
| 2007/0084995 A1 | 4/2007 | Newton et al. |
| 2007/0100226 A1 | 5/2007 | Yankelevitz et al. |
| 2007/0135887 A1 | 6/2007 | Maschke |
| 2007/0142707 A1 | 6/2007 | Wiklof et al. |
| 2007/0156019 A1 | 7/2007 | Larkin et al. |
| 2007/0161893 A1 | 7/2007 | Milner et al. |
| 2007/0161896 A1 | 7/2007 | Adachi et al. |
| 2007/0161963 A1 | 7/2007 | Smalling |
| 2007/0162860 A1 | 7/2007 | Muralidharan et al. |
| 2007/0165141 A1 | 7/2007 | Srinivas et al. |
| 2007/0167710 A1 | 7/2007 | Unal et al. |
| 2007/0167804 A1 | 7/2007 | Park et al. |
| 2007/0191682 A1 | 8/2007 | Rolland et al. |
| 2007/0201736 A1 | 8/2007 | Klingensmith et al. |
| 2007/0206193 A1 | 9/2007 | Pesach |
| 2007/0208276 A1 | 9/2007 | Kornkven Volk et al. |
| 2007/0225220 A1 | 9/2007 | Ming et al. |
| 2007/0225590 A1 | 9/2007 | Ramos |
| 2007/0229801 A1 | 10/2007 | Tearney et al. |
| 2007/0232872 A1 | 10/2007 | Prough et al. |
| 2007/0232874 A1 | 10/2007 | Ince |
| 2007/0232890 A1 | 10/2007 | Hirota |
| 2007/0232891 A1 | 10/2007 | Hirota |

(56) References Cited

U.S. PATENT DOCUMENTS

| | | |
|---|---|---|
| 2007/0232892 A1 | 10/2007 | Hirota |
| 2007/0232893 A1 | 10/2007 | Tanioka |
| 2007/0232933 A1 | 10/2007 | Gille et al. |
| 2007/0238957 A1 | 10/2007 | Yared |
| 2007/0247033 A1 | 10/2007 | Eidenschink et al. |
| 2007/0250000 A1 | 10/2007 | Magnin et al. |
| 2007/0250036 A1 | 10/2007 | Volk et al. |
| 2007/0255304 A1 | 11/2007 | Roschak et al. |
| 2007/0258094 A1 | 11/2007 | Izatt et al. |
| 2007/0260138 A1 | 11/2007 | Feldman et al. |
| 2007/0278389 A1 | 12/2007 | Ajgaonkar et al. |
| 2007/0287914 A1 | 12/2007 | Cohen |
| 2008/0002183 A1 | 1/2008 | Yatagai et al. |
| 2008/0013093 A1 | 1/2008 | Izatt et al. |
| 2008/0021275 A1 | 1/2008 | Tearney et al. |
| 2008/0027481 A1 | 1/2008 | Gilson et al. |
| 2008/0043024 A1 | 2/2008 | Schiwietz et al. |
| 2008/0045842 A1 | 2/2008 | Furnish |
| 2008/0051660 A1 | 2/2008 | Kakadaris et al. |
| 2008/0063304 A1 | 3/2008 | Russak et al. |
| 2008/0085041 A1 | 4/2008 | Breeuwer |
| 2008/0095465 A1 | 4/2008 | Mullick et al. |
| 2008/0095714 A1 | 4/2008 | Castella et al. |
| 2008/0097194 A1 | 4/2008 | Milner |
| 2008/0097218 A1 | 4/2008 | Vrba |
| 2008/0101667 A1 | 5/2008 | Begelman et al. |
| 2008/0108867 A1 | 5/2008 | Zhou |
| 2008/0114254 A1 | 5/2008 | Matcovitch et al. |
| 2008/0119739 A1 | 5/2008 | Vardi et al. |
| 2008/0124495 A1 | 5/2008 | Horn et al. |
| 2008/0125772 A1 | 5/2008 | Stone et al. |
| 2008/0139897 A1 | 6/2008 | Ainsworth et al. |
| 2008/0143707 A1 | 6/2008 | Mitchell |
| 2008/0146941 A1 | 6/2008 | Dala-Krishna |
| 2008/0147111 A1 | 6/2008 | Johnson et al. |
| 2008/0154128 A1 | 6/2008 | Milner |
| 2008/0161696 A1 | 7/2008 | Schmitt et al. |
| 2008/0171944 A1 | 7/2008 | Brenneman et al. |
| 2008/0175465 A1 | 7/2008 | Jiang et al. |
| 2008/0177183 A1 | 7/2008 | Courtney et al. |
| 2008/0180683 A1 | 7/2008 | Kemp |
| 2008/0181477 A1 | 7/2008 | Izatt et al. |
| 2008/0187201 A1 | 8/2008 | Liang et al. |
| 2008/0228086 A1 | 9/2008 | Ilegbusi et al. |
| 2008/0247622 A1 | 10/2008 | Aylward et al. |
| 2008/0247716 A1 | 10/2008 | Thomas et al. |
| 2008/0262470 A1 | 10/2008 | Lee et al. |
| 2008/0262489 A1 | 10/2008 | Steinke |
| 2008/0269599 A1 | 10/2008 | Csavoy et al. |
| 2008/0281205 A1 | 11/2008 | Naghavi et al. |
| 2008/0281248 A1 | 11/2008 | Angheloiu et al. |
| 2008/0285043 A1 | 11/2008 | Fercher et al. |
| 2008/0287795 A1 | 11/2008 | Klingensmith et al. |
| 2008/0291463 A1 | 11/2008 | Milner et al. |
| 2008/0292173 A1 | 11/2008 | Hsieh et al. |
| 2008/0294034 A1 | 11/2008 | Krueger et al. |
| 2008/0298655 A1 | 12/2008 | Edwards |
| 2008/0306766 A1 | 12/2008 | Ozeki et al. |
| 2009/0009801 A1 | 1/2009 | Tabuki |
| 2009/0018393 A1 | 1/2009 | Dick et al. |
| 2009/0034813 A1 | 2/2009 | Dikmen et al. |
| 2009/0043191 A1 | 2/2009 | Castella et al. |
| 2009/0046295 A1 | 2/2009 | Kemp et al. |
| 2009/0052614 A1 | 2/2009 | Hempel et al. |
| 2009/0069843 A1 | 3/2009 | Agnew |
| 2009/0079993 A1 | 3/2009 | Yatagai et al. |
| 2009/0088650 A1 | 4/2009 | Corl |
| 2009/0093980 A1 | 4/2009 | Kemp et al. |
| 2009/0122320 A1 | 5/2009 | Petersen et al. |
| 2009/0138544 A1 | 5/2009 | Wegenkittl et al. |
| 2009/0149739 A9 | 6/2009 | Maschke |
| 2009/0156941 A1 | 6/2009 | Moore |
| 2009/0174886 A1 | 7/2009 | Inoue |
| 2009/0174931 A1 | 7/2009 | Huber et al. |
| 2009/0177090 A1 | 7/2009 | Grunwald et al. |
| 2009/0177183 A1 | 7/2009 | Pinkernell et al. |
| 2009/0195514 A1 | 8/2009 | Glynn et al. |
| 2009/0196470 A1 | 8/2009 | Carl et al. |
| 2009/0198125 A1 | 8/2009 | Nakabayashi et al. |
| 2009/0203991 A1 | 8/2009 | Papaioannou et al. |
| 2009/0264768 A1 | 10/2009 | Courtney et al. |
| 2009/0269014 A1 | 10/2009 | Winberg et al. |
| 2009/0270695 A1 | 10/2009 | McEowen |
| 2009/0284322 A1 | 11/2009 | Harrison et al. |
| 2009/0284332 A1 | 11/2009 | Moore et al. |
| 2009/0284749 A1 | 11/2009 | Johnson et al. |
| 2009/0290167 A1 | 11/2009 | Flanders et al. |
| 2009/0292048 A1 | 11/2009 | Li et al. |
| 2009/0299195 A1 | 12/2009 | Muller et al. |
| 2009/0299284 A1 | 12/2009 | Holman et al. |
| 2009/0318951 A1 | 12/2009 | Kashkarov et al. |
| 2009/0326634 A1 | 12/2009 | Vardi |
| 2010/0007669 A1 | 1/2010 | Bethune et al. |
| 2010/0030042 A1 | 2/2010 | Denninghoff et al. |
| 2010/0061611 A1 | 3/2010 | Xu et al. |
| 2010/0063400 A1 | 3/2010 | Hall et al. |
| 2010/0087732 A1 | 4/2010 | Eberle et al. |
| 2010/0094125 A1 | 4/2010 | Younge et al. |
| 2010/0094127 A1 | 4/2010 | Xu |
| 2010/0094135 A1 | 4/2010 | Fang-Yen et al. |
| 2010/0094143 A1 | 4/2010 | Mahapatra et al. |
| 2010/0113919 A1 | 5/2010 | Maschke |
| 2010/0125238 A1 | 5/2010 | Lye et al. |
| 2010/0125268 A1 | 5/2010 | Gustus et al. |
| 2010/0125648 A1 | 5/2010 | Zaharia et al. |
| 2010/0128348 A1 | 5/2010 | Taverner |
| 2010/0152717 A1 | 6/2010 | Keeler |
| 2010/0160788 A1 | 6/2010 | Davies et al. |
| 2010/0161023 A1 | 6/2010 | Cohen et al. |
| 2010/0168714 A1 | 7/2010 | Burke et al. |
| 2010/0179421 A1 | 7/2010 | Tupin |
| 2010/0179426 A1 | 7/2010 | Davies et al. |
| 2010/0220334 A1 | 9/2010 | Condit et al. |
| 2010/0226607 A1 | 9/2010 | Zhang et al. |
| 2010/0234736 A1 | 9/2010 | Corl |
| 2010/0249601 A1 | 9/2010 | Courtney |
| 2010/0256616 A1 | 10/2010 | Katoh et al. |
| 2010/0272432 A1 | 10/2010 | Johnson |
| 2010/0284590 A1 | 11/2010 | Peng et al. |
| 2010/0290693 A1 | 11/2010 | Cohen et al. |
| 2010/0331950 A1 | 12/2010 | Strommer |
| 2011/0010925 A1 | 1/2011 | Nix et al. |
| 2011/0021926 A1 | 1/2011 | Spencer et al. |
| 2011/0025853 A1 | 2/2011 | Richardson |
| 2011/0026797 A1 | 2/2011 | Declerck et al. |
| 2011/0032533 A1 | 2/2011 | Izatt et al. |
| 2011/0034801 A1 | 2/2011 | Baumgart |
| 2011/0044546 A1 | 2/2011 | Pan et al. |
| 2011/0066073 A1 | 3/2011 | Kuiper et al. |
| 2011/0071401 A1 | 3/2011 | Hastings et al. |
| 2011/0072405 A1 | 3/2011 | Chen et al. |
| 2011/0077528 A1 | 3/2011 | Kemp et al. |
| 2011/0080591 A1 | 4/2011 | Johnson et al. |
| 2011/0087104 A1 | 4/2011 | Moore et al. |
| 2011/0137140 A1 | 6/2011 | Tearney et al. |
| 2011/0144502 A1 | 6/2011 | Zhou et al. |
| 2011/0152771 A1 | 6/2011 | Milner et al. |
| 2011/0157597 A1 | 6/2011 | Lu et al. |
| 2011/0160586 A1 | 6/2011 | Li et al. |
| 2011/0166451 A1* | 7/2011 | Blaivas ............... A61B 17/282 600/439 |
| 2011/0178413 A1 | 7/2011 | Schmitt et al. |
| 2011/0190586 A1 | 8/2011 | Kemp |
| 2011/0216378 A1 | 9/2011 | Poon et al. |
| 2011/0220985 A1 | 9/2011 | Son et al. |
| 2011/0238061 A1 | 9/2011 | van der Weide et al. |
| 2011/0238083 A1 | 9/2011 | Moll et al. |
| 2011/0245669 A1 | 10/2011 | Zhang |
| 2011/0249094 A1 | 10/2011 | Wang et al. |
| 2011/0257545 A1 | 10/2011 | Suri |
| 2011/0264125 A1 | 10/2011 | Wilson et al. |
| 2011/0274329 A1 | 11/2011 | Mathew et al. |
| 2011/0282334 A1 | 11/2011 | Groenhoff |
| 2011/0301684 A1 | 12/2011 | Fischell et al. |

(56) References Cited

U.S. PATENT DOCUMENTS

| | | |
|---|---|---|
| 2011/0306995 A1 | 12/2011 | Moberg |
| 2011/0319752 A1 | 12/2011 | Steinberg et al. |
| 2012/0004529 A1 | 1/2012 | Tolkowsky et al. |
| 2012/0004668 A1 | 1/2012 | Wallace et al. |
| 2012/0013914 A1 | 1/2012 | Kemp et al. |
| 2012/0016344 A1 | 1/2012 | Kusakabe |
| 2012/0016395 A1 | 1/2012 | Olson |
| 2012/0022360 A1 | 1/2012 | Kemp |
| 2012/0026503 A1 | 2/2012 | Lewandowski et al. |
| 2012/0029007 A1 | 2/2012 | Graham et al. |
| 2012/0059253 A1 | 3/2012 | Wang et al. |
| 2012/0059368 A1 | 3/2012 | Takaoka et al. |
| 2012/0062843 A1 | 3/2012 | Ferguson et al. |
| 2012/0065481 A1 | 3/2012 | Hunter et al. |
| 2012/0071823 A1 | 3/2012 | Chen |
| 2012/0071838 A1 | 3/2012 | Fojtik |
| 2012/0075638 A1 | 3/2012 | Rollins et al. |
| 2012/0083696 A1 | 4/2012 | Kitamura |
| 2012/0095340 A1 | 4/2012 | Smith |
| 2012/0095372 A1 | 4/2012 | Sverdlik et al. |
| 2012/0108943 A1 | 5/2012 | Bates et al. |
| 2012/0113108 A1 | 5/2012 | Dala-Krishna |
| 2012/0116353 A1 | 5/2012 | Arnold et al. |
| 2012/0130243 A1 | 5/2012 | Balocco et al. |
| 2012/0130247 A1 | 5/2012 | Waters et al. |
| 2012/0136259 A1 | 5/2012 | Milner et al. |
| 2012/0136427 A1 | 5/2012 | Palmaz et al. |
| 2012/0137075 A1 | 5/2012 | Vorbach |
| 2012/0155734 A1 | 6/2012 | Barratt et al. |
| 2012/0158101 A1 | 6/2012 | Stone et al. |
| 2012/0162660 A1 | 6/2012 | Kemp |
| 2012/0165661 A1 | 6/2012 | Kemp et al. |
| 2012/0170848 A1 | 7/2012 | Kemp et al. |
| 2012/0172698 A1 | 7/2012 | Teo et al. |
| 2012/0176607 A1 | 7/2012 | Ott |
| 2012/0184853 A1 | 7/2012 | Waters |
| 2012/0184859 A1 | 7/2012 | Shah et al. |
| 2012/0184977 A1 | 7/2012 | Wolf |
| 2012/0215094 A1 | 8/2012 | Rahimian et al. |
| 2012/0220836 A1 | 8/2012 | Alpert et al. |
| 2012/0220851 A1 | 8/2012 | Razansky et al. |
| 2012/0220865 A1 | 8/2012 | Brown et al. |
| 2012/0220874 A1 | 8/2012 | Hancock et al. |
| 2012/0220883 A1 | 8/2012 | Manstrom et al. |
| 2012/0224751 A1 | 9/2012 | Kemp et al. |
| 2012/0226153 A1 | 9/2012 | Brown et al. |
| 2012/0230565 A1 | 9/2012 | Steinberg et al. |
| 2012/0232400 A1 | 9/2012 | Dickinson et al. |
| 2012/0238869 A1 | 9/2012 | Schmitt et al. |
| 2012/0238956 A1 | 9/2012 | Yamada et al. |
| 2012/0244043 A1 | 9/2012 | Leblanc et al. |
| 2012/0250028 A1 | 10/2012 | Schmitt et al. |
| 2012/0253186 A1 | 10/2012 | Simpson et al. |
| 2012/0253192 A1 | 10/2012 | Cressman |
| 2012/0253276 A1 | 10/2012 | Govari et al. |
| 2012/0257210 A1 | 10/2012 | Whitney et al. |
| 2012/0262720 A1 | 10/2012 | Brown et al. |
| 2012/0265077 A1 | 10/2012 | Gille et al. |
| 2012/0265268 A1 | 10/2012 | Blum et al. |
| 2012/0265296 A1 | 10/2012 | McNamara et al. |
| 2012/0271170 A1 | 10/2012 | Emelianov et al. |
| 2012/0271175 A1 | 10/2012 | Moore et al. |
| 2012/0271339 A1 | 10/2012 | O'Beirne et al. |
| 2012/0274338 A1 | 11/2012 | Baks et al. |
| 2012/0276390 A1 | 11/2012 | Ji et al. |
| 2012/0277722 A1 | 11/2012 | Gerber et al. |
| 2012/0279764 A1 | 11/2012 | Jiang et al. |
| 2012/0283758 A1 | 11/2012 | Miller et al. |
| 2012/0289987 A1 | 11/2012 | Wilson et al. |
| 2012/0299439 A1 | 11/2012 | Huang |
| 2012/0310081 A1 | 12/2012 | Adler et al. |
| 2012/0310332 A1 | 12/2012 | Murray et al. |
| 2012/0319535 A1 | 12/2012 | Dausch |
| 2012/0323075 A1 | 12/2012 | Younge et al. |
| 2012/0323127 A1 | 12/2012 | Boyden et al. |
| 2012/0330141 A1 | 12/2012 | Brown et al. |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0026655 A1 | 1/2013 | Lee et al. |
| 2013/0030295 A1 | 1/2013 | Huennekens et al. |
| 2013/0030303 A1 | 1/2013 | Ahmed et al. |
| 2013/0030410 A1 | 1/2013 | Drasler et al. |
| 2013/0053949 A1 | 2/2013 | Pintor et al. |
| 2013/0109958 A1 | 5/2013 | Baumgart et al. |
| 2013/0109959 A1 | 5/2013 | Baumgart et al. |
| 2013/0137980 A1 | 5/2013 | Waters et al. |
| 2013/0150716 A1 | 6/2013 | Stigall et al. |
| 2013/0158594 A1 | 6/2013 | Carrison et al. |
| 2013/0218201 A1 | 8/2013 | Obermiller et al. |
| 2013/0218267 A1 | 8/2013 | Braido et al. |
| 2013/0223789 A1 | 8/2013 | Lee et al. |
| 2013/0223798 A1 | 8/2013 | Jenner et al. |
| 2013/0296704 A1 | 11/2013 | Magnin et al. |
| 2013/0303907 A1 | 11/2013 | Corl |
| 2013/0303920 A1 | 11/2013 | Corl |
| 2013/0310698 A1 | 11/2013 | Judell et al. |
| 2013/0331820 A1 | 12/2013 | Itou et al. |
| 2013/0338766 A1 | 12/2013 | Hastings et al. |
| 2013/0339958 A1 | 12/2013 | Droste et al. |
| 2014/0039294 A1 | 2/2014 | Jiang |
| 2014/0180067 A1 | 6/2014 | Stigall et al. |
| 2014/0180128 A1 | 6/2014 | Corl |
| 2014/0200438 A1 | 7/2014 | Millett et al. |

FOREIGN PATENT DOCUMENTS

| | | |
|---|---|---|
| EP | 2438877 A2 | 4/2012 |
| GB | 2280261 A | 1/1995 |
| JP | 197330874 A | 3/1973 |
| JP | 2000-262461 A | 9/2000 |
| JP | 2000-292260 A | 10/2000 |
| JP | 2001-125009 A | 5/2001 |
| JP | 2001-272331 A | 10/2001 |
| JP | 2002-374034 A | 12/2002 |
| JP | 2003-143783 A | 5/2003 |
| JP | 2003-172690 A | 6/2003 |
| JP | 2003-256876 A | 9/2003 |
| JP | 2003-287534 A | 10/2003 |
| JP | 2005-274380 A | 10/2005 |
| JP | 2006-184284 A | 7/2006 |
| JP | 2006-266797 A | 10/2006 |
| JP | 2006-313158 A | 11/2006 |
| JP | 2007-024677 A | 2/2007 |
| JP | 2009-233001 A | 10/2009 |
| JP | 2011-56786 A | 3/2011 |
| WO | 91/01156 A1 | 2/1991 |
| WO | 92/16865 A1 | 10/1992 |
| WO | 93/06213 A1 | 4/1993 |
| WO | 93/08829 A1 | 5/1993 |
| WO | 98/38907 A1 | 9/1998 |
| WO | 98/57583 A1 | 12/1998 |
| WO | 00/11511 A1 | 3/2000 |
| WO | 00/044296 A1 | 8/2000 |
| WO | 01/11409 A2 | 2/2001 |
| WO | 03/062802 A2 | 7/2003 |
| WO | 03/073950 A1 | 9/2003 |
| WO | 2004/010856 A1 | 2/2004 |
| WO | 2004/023992 A1 | 3/2004 |
| WO | 2004/096049 A2 | 11/2004 |
| WO | 2005/047813 A1 | 5/2005 |
| WO | 2005/106695 A2 | 11/2005 |
| WO | 2006/029634 A2 | 3/2006 |
| WO | 2006/037132 A1 | 4/2006 |
| WO | 2006/039091 A2 | 4/2006 |
| WO | 2006/061829 A1 | 6/2006 |
| WO | 2006/068875 A2 | 6/2006 |
| WO | 2006/111704 A1 | 10/2006 |
| WO | 2006/119416 A2 | 11/2006 |
| WO | 2006/121851 A2 | 11/2006 |
| WO | 2006/130802 A2 | 12/2006 |
| WO | 2007/002685 A2 | 1/2007 |
| WO | 2007/025230 A2 | 3/2007 |
| WO | 2007/045690 A1 | 4/2007 |

(56) References Cited

FOREIGN PATENT DOCUMENTS

| WO | 2007/058895 A2 | 5/2007 |
|---|---|---|
| WO | 2007/067323 A2 | 6/2007 |
| WO | 2007/084995 A2 | 7/2007 |
| WO | 2008/058084 A2 | 5/2008 |
| WO | 2008/069991 A1 | 6/2008 |
| WO | 2008/107905 A2 | 9/2008 |
| WO | 2009/009799 A1 | 1/2009 |
| WO | 2009/009801 A1 | 1/2009 |
| WO | 2009/046431 A1 | 4/2009 |
| WO | 2009/121067 A1 | 10/2009 |
| WO | 2009/137704 A1 | 11/2009 |
| WO | 2011/06886 A2 | 1/2011 |
| WO | 2011/038048 A1 | 3/2011 |
| WO | 2011/081688 A1 | 7/2011 |
| WO | 2012/003369 A2 | 1/2012 |
| WO | 2012/061935 A1 | 5/2012 |
| WO | 2012/071388 A2 | 5/2012 |
| WO | 2012/087818 A1 | 6/2012 |
| WO | 2012/098194 A1 | 7/2012 |
| WO | 2012/109676 A1 | 8/2012 |
| WO | 2012/130289 A1 | 10/2012 |
| WO | 2012/154767 A2 | 11/2012 |
| WO | 2012/155040 A1 | 11/2012 |
| WO | 2013/033414 A1 | 3/2013 |
| WO | 2013/033415 A2 | 3/2013 |
| WO | 2013/033418 A1 | 3/2013 |
| WO | 2013/033489 A1 | 3/2013 |
| WO | 2013/033490 A1 | 3/2013 |
| WO | 2013/033592 A1 | 3/2013 |
| WO | 2013/126390 A1 | 8/2013 |
| WO | 2014/109879 A1 | 7/2014 |

OTHER PUBLICATIONS

International Search Report and Written Opinion dated Nov. 2, 2012, for International Patent Application No. PCT/US12/53168, filed Aug. 30, 2013 (8 pages).
International Search Report and Written Opinion dated Apr. 14, 2014, for International Patent Application No. PCT/US2013/076148, filed Dec. 18, 2013 (8 pages).
International Search Report and Written Opinion dated Apr. 21, 2014, for International Patent Application No. PCT/US2013/076015, filed Dec. 18, 2013 (7 pages).
International Search Report and Written Opinion dated Apr. 23, 2014, for International Patent Application No. PCT/US2013/075328, filed Dec. 16, 2013 (8 pages).
International Search Report and Written Opinion dated Apr. 29, 2014, for International Patent Application No. PCT/US13/76093, filed Dec. 18, 2013 (6 pages).
International Search Report and Written Opinion dated Apr. 9, 2014, for International Patent Application No. PCT/US13/75089, filed Dec. 13, 2013 (7 pages).
International Search Report and Written Opinion dated Feb. 21, 2014, for International Patent Application No. PCT/US13/76053, filed Dec. 18, 2013 (9 pages).
International Search Report and Written Opinion dated Feb. 21, 2014, for International Patent Application No. PCT/US2013/076965, filed Dec. 20, 2013 (6 pages).
International Search Report and Written Opinion dated Feb. 27, 2014, for International Patent Application No. PCT/US13/75416, filed Dec. 16, 2013 (7 pages).
International Search Report and Written Opinion dated Feb. 28, 2014, for International Patent Application No. PCT/US13/75653, filed Dec. 17, 2013 (7 pages).
International Search Report and Written Opinion dated Feb. 28, 2014, for International Patent Application No. PCT/US13/75990, filed Dec. 18, 2013 (7 pages).
International Search Report and Written Opinion dated Jan. 16, 2009, for International Patent Application No. PCT/US08/78963 filed on Oct. 6, 2008 (7 Pages).
International Search Report and Written Opinion dated Jul. 30, 2014, for International Patent Application No. PCT/US14/21659, filed Mar. 7, 2014 (15 pages).
International Search Report and Written Opinion dated Mar. 10, 2014, for International Patent Application No. PCT/US2013/076212, filed Dec. 18, 2013 (8 pages).
International Search Report and Written Opinion dated Mar. 11, 2014, for International Patent Application No. PCT/US13/76173, filed Dec. 16, 2013 (9 pages).
International Search Report and Written Opinion dated Mar. 11, 2014, for International Patent Application No. PCT/US13/76449, filed Dec. 19, 2013 (9 pages).
International Search Report and Written Opinion dated Mar. 18, 2014, for International Patent Application No. PCT/US2013/076502, filed Dec. 19, 2013 (7 pages).
International Search Report and Written Opinion dated Mar. 18, 2014, for International Patent Application No. PCT/US2013/076788, filed Dec. 20, 2013 (7 pages).
International Search Report and Written Opinion dated Mar. 19, 2014, for International Patent Application No. PCT/US13/75349, filed Dec. 16, 2013 (10 pages).
International Search Report and Written Opinion dated Mar. 19, 2014, for International Patent Application No. PCT/US2013/076587, filed Dec. 19, 2013 (10 pages).
International Search Report and Written Opinion dated Mar. 19, 2014, for International Patent Application No. PCT/US2013/076909, filed Dec. 20, 2013 (7 pages).
International Search Report and Written Opinion dated Mar. 7, 2014, for International Patent Application No. PCT/US2013/076304, filed Dec. 18, 2013 (9 pages).
International Search Report and Written Opinion dated Mar. 7, 2014, for International Patent Application No. PCT/US2013/076480, filed Dec. 19, 2013 (8 pages).
International Search Report and Written Opinion dated Mar. 7, 2014, for International Patent Application No. PCT/US2013/076512, filed Dec. 19, 2013 (8 pages).
International Search Report and Written Opinion dated Mar. 7, 2014, for International Patent Application No. PCT/US2013/076531, filed Dec. 19, 2013 (10 pages).
Jakobovits et al., 1993, Analysis of homozygous mutant chimeric mice:deletion of the immunoglobulin heavy-chain joining region blocks B-cell development and antibody production, PNAS USA 90:2551-255.
Jakobovits et al., 1993, Germ-line transmission and expression of a human-derived yeast artificial chromosome, Nature 362:255-258.
Jang et al., 2002, Visualization of Coronary Atherosclerotic Plaques in Patients Using Optical Coherence Tomography: Comparison With Intravascular Ultrasound, Journal of the American College of Cardiology 39:604-609.
Jiang et al., 1992, Image registration of multimodality 3-D medical images by chamfer matching, Proc. SPIE 1660, Biomedical Image Processing and Three-Dimensional Microscopy, 356-366.
Johnson et al., 1993, Human antibody engineering: Current Opinion in Structural Biology, 3:564-571.
Jones et al., 1986, Replacing the complementarity-determining regions in a human antibody with those from a mouse, Nature, 321:522-525.
Juviler et al., 2008, Anorectal sepsis and fistula-in-ano, Surgical Technology International, 17:139-149.
Karapatis et al., 1998, Direct rapid tooling:a review of current research, Rapid Prototyping Journal, 4(2):77-89.
Karp et al., 2009, The benefit of time-of-flight in PET imaging, J Nucl Med 49:462-470.
Kelly et al., 2005, Detection of Vascular Adhesion Molecule-1 Expression Using a Novel Multimodal Nanoparticle, Circulation Research 96:327-336.
Kemp et al., 2005, Depth Resolved Optic Axis Orientation in Multiple Layered Anisotropic Tissues Measured with Enhanced Polarization Sensitive Optical Coherence Tomography, Optics Express 13(12):4507-4518.
Kersey et al., 1991, Polarization insensitive fiber optic Michelson interferometer, Electron. Lett. 27:518-520.

(56) References Cited

OTHER PUBLICATIONS

Kheir et al., 2012, Oxygen Gas-Filled Microparticles Provide Intravenous Oxygen Delivery, Science Translational Medicine 4(140):1401a88 (10 pages).
Khuri-Yakub et al., 2011, Capacitive micromachined ultrasonic transducers for medical imaging and therapy, J Micromech Microeng. 21(5):054004-054014.
Kirkman, 1991, Technique for flow reduction in dialysis access fistulas, Surg Gyn Obstet, 172(3):231-3.
Kohler et al., 1975, Continuous cultures of fused cells secreting antibody of predefined specificity, Nature, 256:495-7.
Koo et al., 2011, Diagnosis of IschemiaCausing Coronary Stenoses by Noninvasive Fractional Flow Reserve Computed From Coronary Computed Tomographic Angiograms, J Am Coll Cardiol 58(19):1989-1997.
Kozbor et al., 1984, A human hybrid myeloma for production of human monoclonal antibodies, J. Immunol., 133:3001-3005.
Kruth et al., 2003, Lasers and materials in selective laser sintering, Assembly Automation, 23(4):357-371.
Kumagai et al., 1994, Ablation of polymer films by a femtosecond high-peak-power Ti:sapphire laser at 798 nm, Applied Physics Letters, 65(14):1850-1852.
Larin et al., 2002, Noninvasive Blood Glucose Monitoring with Optical Coherence Tomography: a pilot study in human subjects, Diabetes Care, 25(12):2263-7.
Larin et al., 2004, Measurement of Refractive Index Variation of Physiological Analytes using Differential Phase OCT, Proc of SPIE 5325:31-34.
Laufer, 1996, Introduction to Optics and Lasers in Engineering, Cambridge University Press, Cambridge UK:156-162.
Lefevre et al., 2001, Stenting of bifurcation lesions:a rational approach, J. Interv. Cardiol., 14(6):573-585.
Li et al., 2000, Optical Coherence Tomography: Advanced Technology for the Endoscopic Imaging of Barrett's Esophagus, Endoscopy, 32(12):921-930.
Abdi et al., 2010, Principal component analysis, Wiley Interdisciplinary Reviews: Computational Statistics 2:433-459.
Adler et al., 2007, Phase-Sensitive Optical Coherence Tomography at up to 370,000 Lines Per Second Using Buffered Fourier Domain Mode-Locked Lasers, Optics Letters, 32(6):626-628.
Agresti, 1996, Models for Matched Pairs, Chapter 8, An Introduction to Categorical Data Analysis, Wiley-Interscience A John Wiley & Sons, Inc., Publication, Hoboken, New Jersey.
Akasheh et al., 2004, Development of piezoelectric micromachined ultrasonic transducers, Sensors and Actuators A Physical, 111:275-287.
Amini et al., 1990, Using dynamic programming for solving variational problems in vision, IEEE Transactions on Pattern Analysis and Machine Intelligence, 12(9):855-867.
Bail et al., 1996, Optical coherence tomography with the "Spectral Radar"—Fast optical analysis in volume scatterers by short coherence interferometry, Optics Letters 21(14):1087-1089.
Bain, 2011, Privacy protection and face recognition, Chapter 3, Handbook of Face Recognition, Stan et al., Springer-Verlag.
Barnea et al., 1972, A class of algorithms for fast digital image registration, IEEE Trans. Computers, 21(2):179-186.
Blanchet et al., 1993, Laser Ablation and the Production of Polymer Films, Science, 262(5134):719-721.
Bonnema, 2008, Imaging Tissue Engineered Blood Vessel Mimics with Optical Tomography, College of Optical Sciences dissertation, University of Arizona (252 pages).
Bouma et al., 1999, Power-efficient nonreciprocal interferometer and linear-scanning fiber-optic catheter for optical coherence tomography, Optics Letters, 24(8):531-533.
Breiman, 2001, Random forests, Machine Learning 45:5-32.
Brown, 1992, A survey of image registration techniques, ACM Computing Surveys 24(4):325-376.
Bruining et al., 2009, Intravascular Ultrasound Registration/Integration with Coronary Angiography, Cardiology Clinics, 27(3):531-540.
Brummer, 1997, An euclidean distance measure between covariance matrices of speechcepstra for text-independent speaker recognition, in Proc. South African Symp. Communications and Signal Processing:167-172.
Burr et al., 2005, Searching for the Center of an Ellipse in Proceedings of the 17th Canadian Conference on Computational Geometry:260-263.
Canny, 1986, A computational approach to edge detection, IEEE Trans. Pattern Anal. Mach. Intell. 8:679-698.
Cavalli et al., 2010, Nanosponge formulations as oxygen delivery systems, International Journal of Pharmaceutics 402:254-257.
Choma et al., 2003, Sensitivity Advantage of Swept Source and Fourier Domain Optical Coherence Tomography, Optics Express 11(18):2183-2189.
Clarke et al., 1995, Hypoxia and myocardial ischaemia during peripheral angioplasty, Clinical Radiology, 50(5):301-303.
Collins, 1993, Coronary flow reserve, British Heart Journal 69:279-281.
Communication Mechanisms for Distributed Real-Time Applications, NI Developer Zone, http://zone.ni.eom/devzone/cda/tut/p/id/3105, accessed Jul. 23, 2007.
Cook, 2007, Use and misuse of receiver operating characteristic curve in risk prediction, Circulation 115(7):928-35.
D'Agostino et al., 2001, Validation of the Framingham coronary heart disease prediction score: results of a multiple ethnic group investigation, JAMA 286:180-187.
David et al., 1974, Protein iodination with solid-state lactoperoxidase, Biochemistry 13:1014-1021.
Davies et al., 1985, Plaque fissuring-the cause of acute myocardial infarction, sudden ischaemic death, and crescendo angina, British Heart Journal 53:363-373.
Davies et al., 1993, Risk of thrombosis in human atherosclerotic plaques: role of extracellular lipid, macrophage, and smooth muscle cell content, British Heart Journal 69:377-381.
Deterministic Data Streaming in Distributed Data Acquisition Systems, NI Developer Zone, "What is Developer Zone?", http://zone.ni.eom/devzone/cda/tut/p/id/3105, accessed Jul. 23, 2007.
Eigenwillig, 2008, K-Space Linear Fourier Domain Mode Locked Laser and Applications for Optical Coherence Tomography, Optics Express 16(12):8916-8937.
Elghanian et al., 1997, Selective colorimetric detection of polynucleotides based on the distance-dependent optical properties of gold nanoparticles, Science, 277(5329):1078-1080.
Ergun et al., 2003, Capacitive Micromachined Ultrasonic Transducers:Theory and Technology, Journal of Aerospace Engineering, 16(2):76-84.
Evans et al., 2006, Optical coherence tomography to identify intramucosa carcinoma and high-grade dysplasia in Barrett's esophagus, Clin Gast Hepat 4(1):38-43.
Fatemi et al., 1999, Vibro-acoustography: an imaging modality based on ultrasound-stimulated acoustic emission, PNAS U.S.A., 96(12):6603-6608.
Felzenszwalb et al., 2005, Pictorial Structures for Object Recognition, International Journal of Computer Vision, 61(1):55-79.
Ferring et al., 2008, Vasculature ultrasound for the pre-operative evaluation prior to arteriovenous fistula formation for haemodialysis: review of the evidence, Nephrol. Dial. Transplant. 23(6):1809-1815.
Fischler et al., 1973, The representation and matching of pictorial structures, IEEE Transactions on Computer 22:67-92.
Fleming et al., 2010, Real-time monitoring of cardiac radio-frequency ablation lesion formation using an optical coherence tomography forward-imaging catheter, Journal of Biomedical Optics 15 (3):030516-1 (3 pages).
Fookes et al., 2002, Rigid and non-rigid image registration and its association with mutual information:A review, Technical Report ISBN:1 86435 569 7, RCCVA, QUT.
Forstner & Moonen, 1999, A metric for covariance matrices, In Technical Report of the Dpt of Geodesy and Geoinformatics, Stuttgart University, 113-128.
Goel et al., 2006, Minimally Invasive Limited Ligation Endoluminal-assisted Revision (MILLER) for treatment of dialysis access-associated steal syndrome, Kidney Int 70(4):765-70.

(56) References Cited

OTHER PUBLICATIONS

Gotzinger et al., 2005, High speed spectral domain polarization sensitive optical coherence tomography of the human retina, Optics Express 13(25):10217-10229.
Gould et al., 1974, Physiologic basis for assessing critical coronary stenosis, American Journal of Cardiology, 33:87-94.
Griffiths et al., 1993, Human anti-self antibodies with high specificity from phage display libraries, The EMBO Journal, 12:725-734.
Griffiths et al., 1994, Isolation of high affinity human antibodies directly from large synthetic repertoires, The EMBO Journal, 13(14):3245-3260.
Grund et al., 2010, Analysis of biomarker data:logs, odds, ratios and ROC curves, Curr Opin HIV AID 5(6):473-479.
Harrison et al., 2011, Guidewire Stiffness: What's in a name?, J Endovasc Ther, 18(6):797-801.
Huber et al., 2005, Amplified, Frequency Swept Lasers for Frequency Domain Reflectometry and OCT Imaging: Design and Scaling Principles, Optics Express 13(9):3513-3528.
Huber et al., 2006, Fourier Domain Mode Locking (FDML): A New Laser Operating Regime and Applications for Optical Coherence Tomography, Optics Express 14(8):3225-3237.
International Search Report and Written Opinion dated Mar. 11, 2014, for International Patent Application No. PCT/US13/75675, filed Dec. 17, 2013 (7 pages).
International Search Report and Written Opinion dated Mar. 19, 2014, for International Patent Application No. PCT/US13/075353, filed Dec. 16, 2013 (8 pages).
Little et al., 1991, The underlying coronary lesion in myocardial infarction:implications for coronary angiography, Clinical Cardiology, 14(11):868-874.
Loo, 2004, Nanoshell Enabled Photonics-Based Imaging and Therapy of Cancer, Technology in Cancer Research & Treatment 3(1):33-40.
Machine translation of JP 2000-097846.
Machine translation of JP 2000-321034.
Machine translation of JP 2000-329534.
Machine translation of JP 2004-004080.
Maintz et al., 1998, An Overview of Medical Image Registration Methods, Technical Report UU-CS, (22 pages).
Mamas et al., 2010, Resting Pd/Pa measured with intracoronary pressure wire strongly predicts fractional flow reserve, Journal of Invasive Cardiology 22(6):260-265.
Marks et al., 1991, By-passing Immunization Human Antibodies from V-gene Libraries Displayed on Phage, J. Mol. Biol. 222:581-597.
Marks et al., 1992, By—Passing Immunization:Building High Affinity Human Antibodies by Chain Shuffling, BioTechnol., 10:779-783.
Maruno et al., 1991, Fluorine containing optical adhesives for optical communications systems, J. Appl. Polymer. Sci. 42:2141-2148.
McCafferty et al., 1990, Phage antibodies: filamentous phage displaying antibody variable domains, Nature 348:552-554.
Mendieta et al., 1996, Complementary sequence correlations with applications to reflectometry studies, Instrumentation and Development 3(6):37-46.
Mickley, 2008, Steal Syndrome-strategies to preserve vascular access and extremity, Nephrol Dial Transplant 23:19-24.
Miller et al., 2010, The MILLER banding procedure is an effective method for treating dialysis-associated steal syndrome, Kidney International 77:359-366.
Milstein et al., 1983, Hybrid hybridomas and their use in immunohistochemistry, Nature 305:537-540.
Mindlin et al., 1936, A force at a point of a semi-infinite solid, Physics, 7:195-202.
Morrison et al., 1984, Chimeric human antibody molecules: mouse antigen-binding domains with human constant region domains, PNAS 81:6851-6855.
Munson et al., 1980, Ligand: a versatile computerized approach for characterization of ligand-binding systems, Analytical Biochemistry, 107:220-239.
Nezam, 2008, High Speed Polygon-Scanner-Based Wavelength-Swept Laser Source in the Telescope-Less Configurations with Application in Optical Coherence Tomography, Optics Lettrs 33(15):1741-1743.
Nissen, 2001, Coronary Angiography and Intravascular Ultrasound, American Journal of Cardiology, 87 (suppl):15A-20A.
Nitenberg et al., 1995, Coronary vasdcular reserve in humans: a critical review of methods of evaluation and of interpretation of the results, Eur Heart J. 16(Suppl 1):7-21.
Notice of Reason(s) for Refusal dated Apr. 30, 2013, for Japanese Patent Application No. 2011-508677 for Optical Imaging Catheter for Aberation Balancing to Volcano Corporation, which application is a Japanese national state entry of PCT/US2009/043181 with international filing date May 7, 2009, of the same title, published on Nov. 12, 2009 as WO 2009/137704, and accompanying English translation of the Notice of Reason(s) for Refusal and machine translations of JP11-56786 and JP2004-290548 (56 pages).
Nygren, 1982, Conjugation of horseradish peroxidase to Fab fragments with different homobifunctional and heterobifunctional cross-linking reagents. A comparative study, J. Histochem. and Cytochem. 30:407-412.
Oesterle et al., 1986, Angioplasty at coronary bifurcations: single-guide, two-wire technique, Cathet Cardiovasc Diagn., 12:57-63.
Okuno et al., 2003, Recent Advances in Optical Switches Using Silica-based PLC Technology, NTT Technical Review 1(7):20-30.
Oldenburg et al., 1998, Nanoengineering of Optical Resonances, Chemical Physics Letters 288:243-247.
Oldenburg et al., 2003, Fast-Fourier-Domain Delay Line for In Vivo Optical Coherence Tomography with a Polygonal Scanner, Applied Optics, 42(22):4606-4611.
Othonos, 1997, Fiber Bragg gratings, Review of Scientific Instruments 68(12):4309-4341.
Owens et al., 2007, A Survey of General-Purpose Computation on Graphics Hardware, Computer Graphics Forum 26(1):80-113.
Pain et al., 1981, Preparation of protein A-peroxidase mono conjugate using a heterobifunctional reagent, and its use in enzyme immunoassays, J Immunol Methods, 40:219-30.
Park et al., 2005, Real-time fiber-based multi-functional spectral-domain optical coherence tomography at 1.3 um., Optics Express 13(11):3931-3944.
Pasquesi et al., 2006, In vivo detection of exercise induced ultrastructural changes in genetically-altered murine skeletal muscle using polarization-sensitive optical coherence tomography, Optics Express 14(4):1547-1556.
Pepe et al., 2004, Limitations of the odds ratio in gauging the performance of a diagnostic, prognostic, or screening marker, American Journal of Epidemiology 159(9):882-890.
Persson et al., 1985, Acoustic impedance matching of medical ultrasound transducers, Ultrasonics, 23(2):83-89.
Placht et al., 2012, Fast time-of-flight camera based surface registration for radiotherapy patient positioning, Medical Physics 39(1):4-17.
Rabbani et al., 1999, Review: Strategies to achieve coronary arterial plaque stabilization, Cardiovascular Research 41:402-417.
Radvany et al., 2008, Plaque Excision in Management of Lower Extremity Peripheral Arterial Disease with the SilverHawk Atherectomy Catheter, Seminars in Interventional Radiology, 25(1):11-19.
Reddy et al., 1996, An FFT-Based Technique for Translation, Rotation, and Scale-Invariant Image Registration, IEEE Transaction on Image Processing 5(8):1266-1271.
Riechmann et al., 1988, Reshaping human antibodies for therapy, Nature, 332:323-327.
Rivers et al., 1992, Correction of steal syndrome secondary to hemodialysis access fistulas: a simplified quantitative technique, Surgery, 112(3):593-7.
Robbin et al., 2002, Hemodialysis Arteriovenous Fistula Maturity: US Evaluation, Radiology 225:59-64.
Rollins et al., 1998, In vivo video rate optical coherence tomography, Optics Express 3:219-229.
Sarunic et al., 2005, Instantaneous Complex Conjugate Resolved Spectral Domain and Swept-Source OCT Using 3×3 Fiber Couplers, Optics Express 13(3):957-967.

(56) References Cited

OTHER PUBLICATIONS

Satiani et al., 2009, Predicted Shortage of Vascular Surgeons in the United States, J. Vascular Surgery 50:946-952.
Schneider et al., 2006, T-banding: A technique for flow reduction of a hyper-functioning arteriovenous fistula, J Vasc Surg. 43(2):402-405.
Sen et al., 2012, Development and validation of a new adenosine-independent index of stenosis severity from coronary wave-intensity analysis, Journal of the American College of Cardiology 59(15):1392-1402.
Setta et al., 2005, Soft versus firm embryo transfer catheters for assisted reproduction: a systematic review and meta-analysis, Human Reproduction, 20(11):3114-3121.
Seward et al., 1996, Ultrasound Cardioscopy: Embarking on New Journey, Mayo Clinic Proceedings 71(7):629-635.
Shen et al., 2006, Eigengene-based linear discriminant model for tumor classification using gene expression microarray data, Bioinformatics 22(21):2635-2642.
Sihan et al., 2008, A novel approach to quantitative analysis of intraluminal optical coherence tomography imaging, Comput. Cardiol:1089-1092.
Siwy et al., 2003, Electro-responsive asymmetric nanopores in polyimide with stable ion-current signal, Applied Physics A: Materials Science & Processing 76:781-785.
Smith et al., 1989, Absolute displacement measurements using modulation of the spectrum of white light in a Michelson interferometer, Applied Optics, 28(16):3339-3342.
Smith, 1997, The Scientist and Engineer's Guide to Digital Signal Processing, California Technical Publishing, San Diego, CA:432-436.
Soller, 2003, Polarization diverse optical frequency domain interferonnetry:All coupler implementation, Bragg Grating, Photosensitivity, and Poling in Glass Waveguides Conference MB4:30-32.
Song et al., 2012, Active tremor cancellation by a "Smart" handheld vitreoretinal microsurgical tool using swept source optical coherence tomography, Optics Express, 20(21):23414-23421.
Stenqvist et al., 1983, Stiffness of central venous catheters, Acta Anaesthesiol Scand., 2:153-157.
Strickland, 1970, Time-Domain Reflectometer Measurements, Tektronix, Beaverton, OR, (107 pages).
Strobl et al., 2009, An Introduction to Recursive Partitioning:Rationale, Application and Characteristics of Classification and Regression Trees, Bagging and Random Forests, Psychol Methods., 14(4):323-348.
Sutcliffe et al., 1986, Dynamics of UV laser ablation of organic polymer surfaces, Journal of Applied Physics, 60(9):3315-3322.
Suzuki, 2013, A novel guidewire approach for handling acute-angle bifurcations, J Inv Cardiol 25(1):48-54.
Tanimoto et al., 2008, A novel approach for quantitative analysis of intracoronary optical coherence tomography: high inter-observer agreement with computer-assisted contour detection, Cathet Cardiovascular Intervent., 72(2):228-235.
Tearney et al., 1997, In vivo Endoscopic Optical Biopsy with Optical Coherence Tomography, Science, 276:2037-2039.
Tonino et al., 2009, Fractional flow reserve versus angiography for guiding percutaneous coronary intervention, The New England Journal of Medicine, 360:213-224.
Toregeani et al., 2008, Evaluation of hemodialysis arteriovenous fistula maturation by color-flow Doppler ultrasound, J Vasc. Bras. 7(3):203-213.
Translation of Notice of Reason(s) for Refusal dated Apr. 30, 2014, for Japanese Patent Application No. 2011-508677, (5 pages).
Translation of Notice of Reason(s) for Refusal dated May 25, 2012, for Japanese Patent Application No. 2009-536425, (3 pages).
Translation of Notice of Reason(s) for Refusal dated Nov. 22, 2012, for Japanese Patent Application No. 2010-516304, (6 pages).
Traunecker et al., 1991, Bispecific single chain molecules (Janusins) target cytotoxic lymphocytes on HIV infected cells, EMBO J., 10:3655-3659.
Trolier-McKinstry et. al., 2004, Thin Film Piezoelectric for MEMS, Journal of Electroceramics 12:7-17.
Tuniz et al., 2010, Weaving the invisible thread: design of an optically invisible metamaterial fibre, Optics Express 18(17):18095-18105.
Turk et al., 1991, Eigenfaces for Recognition, Journal of Cognitive Neuroscience 3(1):71-86.
Tuzel et al., 2006, Region Covariance: A Fast Descriptor for Detection and Classification, European Conference on Computer Vision (ECCV).
Urban et al., 2010, Design of a Pressure Sensor Based on Optical Bragg Grating Lateral Deformation, Sensors (Basel), 10(12):11212-11225.
Vakhtin et al., 2003, Common-path interferometer for frequency-domain optical coherence tomography, Applied Optics, 42(34):6953-6958.
Vakoc et al., 2005, Phase-Resolved Optical Frequency Domain Imaging, Optics Express 13(14):5483-5493.
Verhoeyen et al., 1988, Reshaping human antibodies: grafting an antilysozyme activity, Science, 239:1534-1536.
Villard et al., 2002, Use of a blood substitute to determine instantaneous murine right ventricular thickening with optical coherence tomography, Circulation, 105:1843-1849.
Wang et al., 2002, Optimizing the Beam Patten of a Forward-Viewing Ring-Annular Ultrasound Array for Intravascular Imaging, Transactions on Ultrasonics, Ferroelectrics, and Frequency Control, 49(12).
Wang et al., 2006, Multiple biomarkers for the prediction of first major cardiovascular events and death, The New England Journal of Medicine, 355(25):2631-2639.
Wang et al., 2009, Robust Guidewire Tracking in Fluoroscopy, IEEE Conference on Computer Vision and Pattern Recognition—CVPR 2009:691-698.
Wang et al., 2011, In vivo intracardiac optical coherence tomography imaging through percutaneous access: toward image-guided radio-frequency ablation, J. Biomed. Opt. 0001 16(11):110505-1 (3 pages).
Waterhouse et. al., 1993, Combinatorial infection and in vivo recombination: a strategy for making large phage antibody repertoires, Nucleic Acids Res., 21:2265-2266.
Wegener, 2011, 3D Photonic Metamaterials and Invisibility Cloaks: The Method of Making, MEMS 2011, Cancun, Mexico, Jan. 23-27, 2011.
West et al., 1991, Arterial insufficiency in hemodialysis access procedures: correction by banding technique, Transpl Proc 23(2):1838-40.
Wyawahare et al., 2009, Image registration techniques: an overview, International Journal of Signal Processing, Image Processing and Pattern Recognition, 2(3):11-28.
Yaqoob et al., 2006, Methods and application areas of endoscopic optical coherence tomography, J. Biomed. Opt., 11, 063001-1-063001-19.
Yasuno et al., 2004, Polarization-sensitive complex Fourier domain optical coherence tomography for Jones matrix imaging of biological samples, Applied Physics Letters 85(15):3023-3025.
Zhang et al., 2004, Full range polarization-sensitive Fourier domain optical coherence tomography, Optics Express, 12(24):6033-6039.
Zitova et al., 2003, Image registration methods: A survey. Image and Vision Computing, 21(11):977-1000.

\* cited by examiner

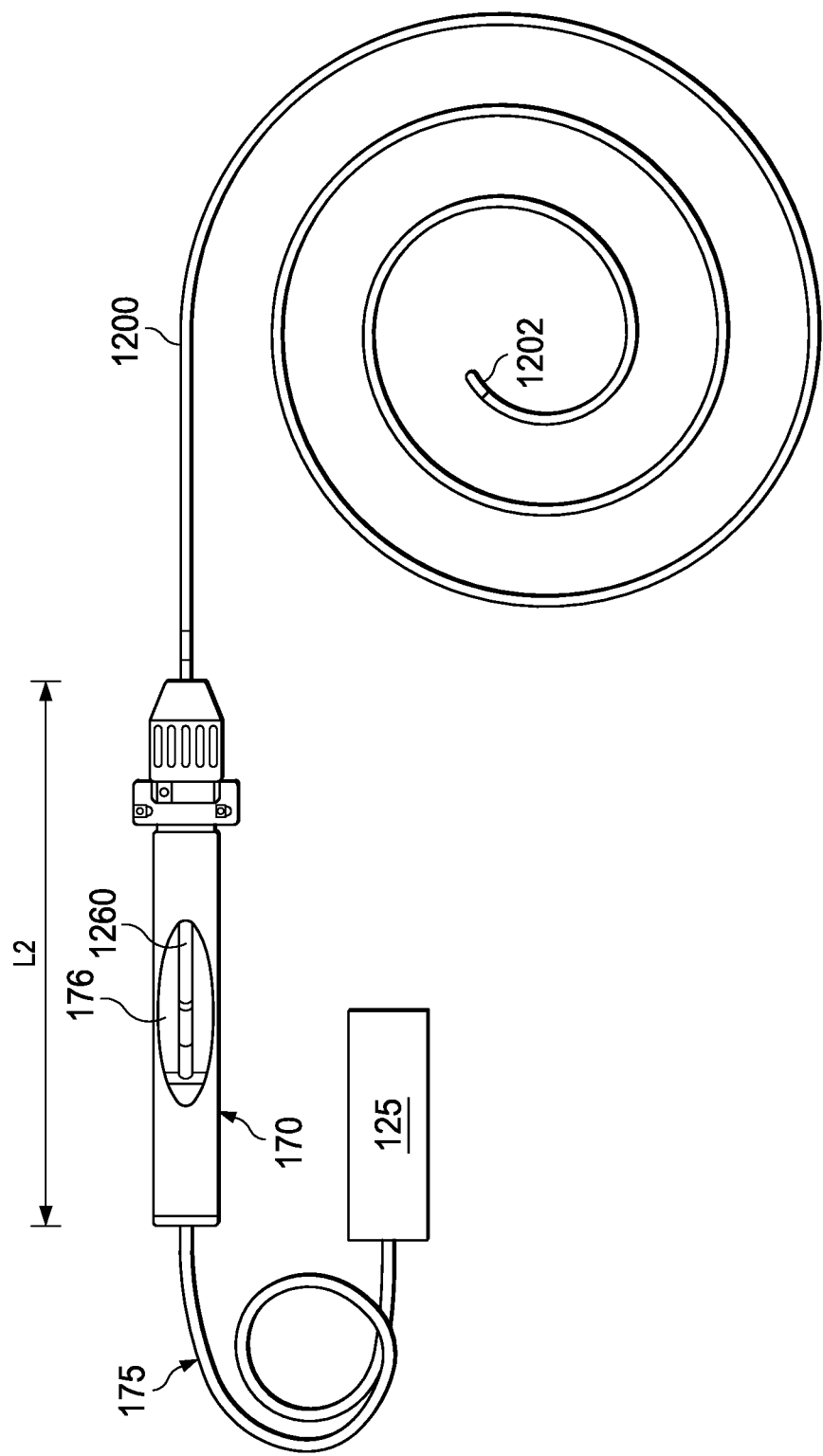

DEVICES, SYSTEMS, AND METHODS FOR TARGETED CANNULATION

CROSS-REFERENCE TO RELATED APPLICATIONS

The present application claims priority to and the benefit of U.S. Provisional Patent Application No. 61/737,022, filed Dec. 13, 2012, and U.S. Provisional Patent Application No. 61/737,040, filed Dec. 13, 2012, each of which is hereby incorporated by reference in its entirety.

BACKGROUND

During a variety of medical procedures, including vascular cannulation, it is desirable to intentionally penetrate certain internal anatomic structures to facilitate diagnostic and therapeutic objectives. However, accurate and efficient penetration may be difficult to accomplish, and may be accompanied by risks of inadvertently altering and/or harming neighboring structures.

For example, a common procedure involving external to internal penetration of an anatomic structure is the localization and cannulation of vessels for inserting intravenous ("IV") tubes, drawing blood, or inserting an arterial catheter. However, health care practitioners may have difficulty in accurately locating the target vessel before advancing the delivery instrument or needle into the patient's tissue. Multiple placement attempts can result in discomfort to the patient and prolong the procedure time. In some instances, multiple placement attempts can damage neighboring structures such as nerves and other vessels. This problem is particularly pronounced in pediatric patients, obese patients, patients with unusual anatomy, and in acute care situations such as an emergency.

Various devices and methods have been devised to help healthcare practitioners accurately locate a vessel prior to cannulation. For example, some methods employ Doppler sonar technology to determine the location and direction of the target vessel. However, several of these methods involve insertion of a needle into the patient's subcutaneous tissue before using Doppler to accurately locate the target vessel. The user employs a sweeping motion within the patient's tissue to locate the target vessel. Such a sweeping motion may be painful to the patient and cause injury to neighboring structures. Moreover, some ultrasonic placement devices require complicated catheter construction that incorporates ultrasonic transducers and receivers in the delivery instrument.

The devices, systems, and methods disclosed herein overcome one or more of the deficiencies of the prior art.

SUMMARY

The present disclosure provides devices, systems, and methods for accessing and evaluating a vessel in a patient in a safe and accurate manner. The devices, systems, and methods can utilize Doppler ultrasound sensing to guide a user to the vessel and confirm positioning within the blood vessel. Once access to the vessel has been obtained in a safe and accurate manner, any number of alternative sensing devices can be introduced into the vessel for additional diagnosis and/or treatment.

In one exemplary embodiment, the present disclosure describes a system for accessing and evaluating a blood vessel in a patient. The system comprises an access sensor wire, an access needle sized to receive the access sensor wire, and a second sensing wire configured to be sequentially positioned within the access needle. In one feature, the access sensor wire includes a rigid member having a length generally equivalent to the length of the access needle while the second sensing wire is very flexible and several times longer than the access needle. A method is also disclosed for utilizing a short access sensing wire to access a blood vessel with in an introduction needle with the short access sensing wire being replaced by a much longer second sensing wire after the needle is positioned in the vessel. In one embodiment, both the access sensing wire and second sensing wire having a substantially similar connection assembly.

In another exemplary embodiment, the present disclosure is directed to a system for blood vessel access and sensing in a patient. The system comprises a first access sensor wire having a hollow, elongate tube with a first length and first outer diameter, and a sensor disposed adjacent a distal portion of the tube configured to transmit and receive waves to detect Doppler shift. The system further includes a hollow penetrating instrument including a lumen defining a first inner diameter extending to a sharp distal end, the second lumen sized and shaped to receive the sensor wire. In one aspect, the system also includes a second sensor wire having a second length and a second outer diameter, wherein the second length is greater than two times the first length and the second outer diameter is substantially equal to the first diameter and configured for passing through the lumen of the hollow penetrating instrument. In one embodiment, the elongate tube is a rigid member.

In another aspect, the present disclosure provides a system for blood vessel access and sensing in a patient including a connection mechanism for outputting sensor data to a processing system. In one aspect, the system includes a first access sensor wire having a hollow, elongate tube with a first length and first outer diameter configured for passing through a lumen of a hollow blood vessel penetrating instrument, and a sensor disposed adjacent a distal portion of the tube configured to transmit and receive waves to detect Doppler shift, the sensor in communication with a first connection assembly disposed adjacent a proximal portion of the tube. In a further aspect, the system includes a second sensor wire having a second length and a second outer diameter, wherein the second length is greater than two times the first length and the second outer diameter is substantially equal to the first diameter and configured for passing through the lumen of the hollow penetrating instrument, the second sensor wire having a second connection assembly disposed adjacent a proximal portion of the wire, the second connection assembly configured to substantially match the first connection assembly. The system may also include a female connector coupled to a signal processing system configured to analyze data from the sensor to detect a Doppler shift, the female connector having a lumen configured to receive each of the first connection assembly and second connection assembly sequentially. In one embodiment, the elongate tube is sufficiently rigid to maintain the connection assembly in alignment with the lumen of the hollow penetrating instrument when coupled to the female connector.

In still a further aspect, the present disclosure provides a method of accessing a vessel in a patient and sensing a parameter of a patient from within a connected vessel. In an exemplary form, the method comprises connecting a sensor wire communication connection assembly to a female connector interconnected with a signal processing system; inserting the sensor wire into a lumen of a penetrating instrument, wherein the sensor wire includes a Doppler ultrasound transducer at a distal portion of the sensor wire, and wherein the penetrating instrument includes a sharp distal tip. The method continues by positioning the distal portion of the sensor wire adjacent the sharp distal tip of the penetrating instrument, positioning the distal portion of the sensor wire adjacent a skin surface of the patient, analyzing the Doppler shift of the reflected ultrasound data to evaluate the presence of a vessel in the tissue and the direction of flow within the vessel, moving the penetrating instrument and the sensor wire on the skin surface and analyzing the reflected ultrasound data until an optimal position and angle for penetrating the vessel is identified, and advancing the penetrating instrument into the skin surface and penetrating the vessel. Once the vessel has been accessed, then removing the access sensor wire from the penetrating instrument, connecting an internal sensor wire communication connection assembly to the female connector interconnected with the signal processing system, and inserting the internal sensor wire through the penetrating instrument into a blood vessel.

In another exemplary embodiment, the present disclosure describes sensor wire that can be utilized within an introduction needle to identify blood vessels. In one embodiment, the sensor wire includes a rigid tubular body that can maintain the distal sensor in substantial alignment with the proximal communication connection assembly, even when carrying the weight of a female connector. In a further aspect, the sensing wire is relatively short in relation to its diameter. In still a further feature, the communication connection assembly has a length that is about 10 percent of the overall length of the sensing wire. In still a further feature, the sensing wire has a substantially uniform diameter from the distal sensor up to and including the communication connection assembly.

In another exemplary embodiment, the present disclosure is directed to a device for locating a blood vessel in a patient. In one aspect, the device includes a hollow, elongate rigid tube including a lumen extending from a proximal portion to a distal portion, the tube having a longitudinal axis; an ultrasonic sensor coupled to the distal portion, the sensor configured to transmit and receive ultrasound waves distally along the longitudinal axis to detect Doppler shift; and at least one communication line extending from the sensor to a communication connection assembly positioned adjacent the proximal portion, wherein the rigid tube maintains the ultrasonic sensor and communication connection assembly in substantial alignment with the longitudinal axis during use.

In a further exemplary embodiment, the present disclosure is directed to a device for locating a blood vessel in a patient. The device comprises a sensor wire having a hollow, elongate tube including a lumen extending from a proximal portion to a distal portion, and having a length and a diameter wherein the length is less than 1000 times the diameter. The sensor wire includes an ultrasonic sensor positioned adjacent the distal portion and configured to transmit and receive ultrasound waves to detect Doppler shift and a communication connection assembly positioned adjacent the proximal portion. A further feature includes a hollow connector having a weight and configured to couple the sensor wire to a Doppler ultrasound processor, wherein the connector includes a second lumen sized to receive the communication connection assembly.

In still a further exemplary embodiment, the present disclosure provides a device for locating a blood vessel. The device includes a sensing wire tube having a first length extending along longitudinal axis and a diameter. The sensing wire includes a hollow, elongate tube including a lumen extending from a proximal portion to a distal portion, an ultrasonic sensor coupled to the distal portion, the sensor configured to transmit and receive ultrasound waves distally along the longitudinal axis to detect Doppler shift, and a least one communication line extending from the sensor to a communication connection assembly positioned adjacent the proximal portion. In at least one example, the connection assembly having a second length, wherein the ratio of the first length to the second length is less than 10 to 1. In still a further aspect, the sensor wire includes a pressure sensor for sensing blood pressure once the device is inserted into the body of a patient.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

FIG. 12 illustrates a partial cutaway side-view of an elongated sensor wire coupled to a connector according to one embodiment of the present disclosure.

DETAILED DESCRIPTION

Figure 1:
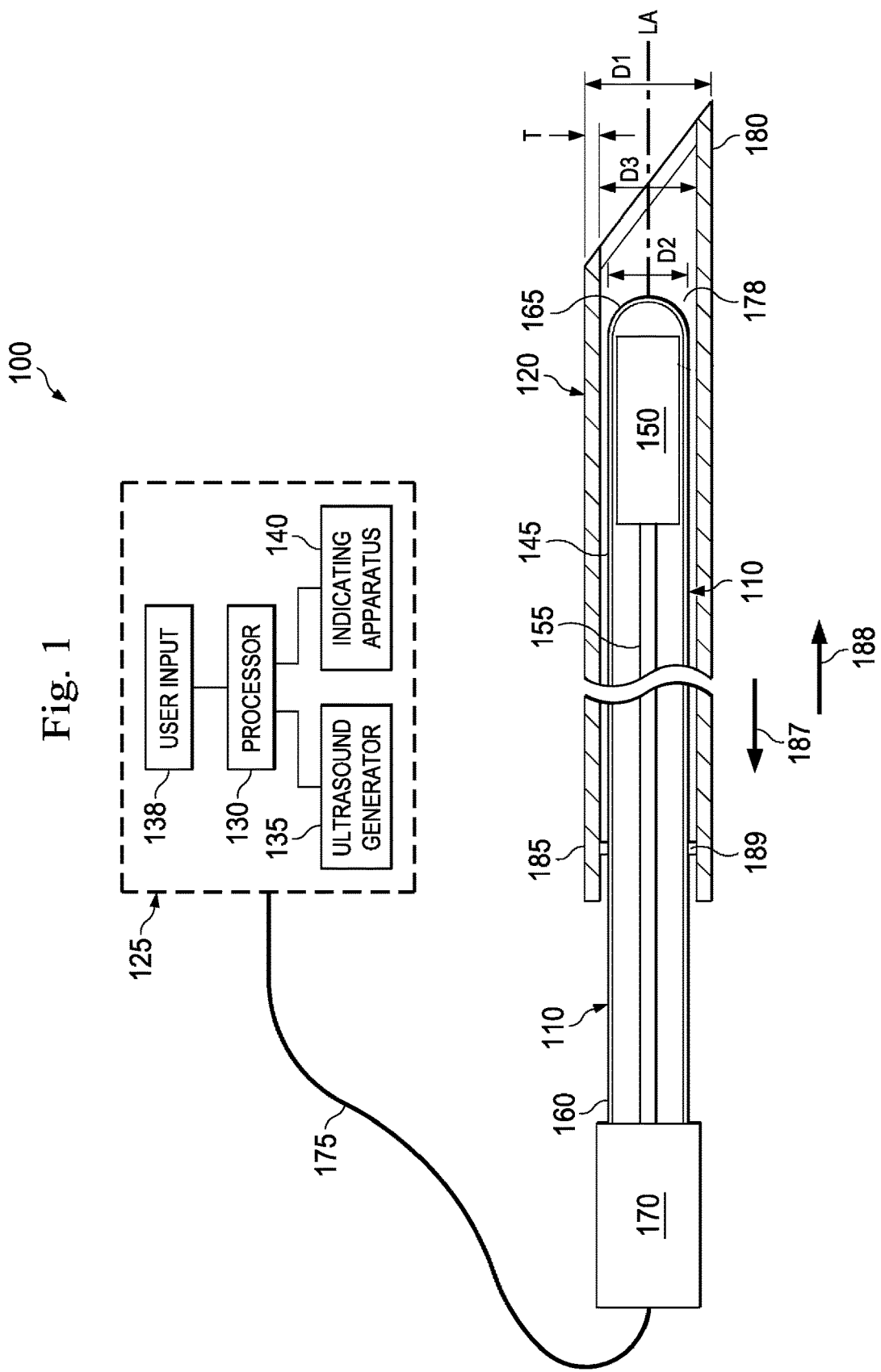
FIG. 1 is a schematic illustration of a cannulation system according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, for the sake of brevity, the various embodiments of prosthetic devices and corresponding engagement structures are described below with reference to particular exemplary combinations of components, features, and structures. However, it is understood that the various components, features, and structures of the exemplary embodiments are combinable in numerous other ways. It is fully contemplated that the features, components, and/or steps described with respect to one embodiment may be combined with the features, components, and/or steps described with respect to other embodiments of the present disclosure. Thus, features from one embodiment may be combined with features from another embodiment to form yet another embodiment of a device, system, or method according to the present disclosure even though such a combination is not explicitly shown. Further, for the sake of simplicity, in some instances the same reference numbers are used throughout the drawings to refer to the same or like parts.

The present disclosure relates to devices, systems, and methods for accurately locating and penetrating anatomic structures using ultrasonic Doppler technology. More particularly, but not by way of limitation, the present disclosure relates to an ultrasonic sensor wire that is sized, shaped, and configured to pass through a penetrating instrument and transmit an ultrasound signal through the skin of the patient towards the region of a target vessel, thereby indicating the accurate location and direction of the target vessel. In addition, the present disclosure relates to a cannulation system comprising a sensor wire, a penetrating instrument, and a Doppler ultrasound system to allow the user to determine the location and direction of the target vessel in real time before and while advancing the penetrating instrument into the patient's body. Moreover, the present disclosure provides for a sensor wire that includes a protective sheath designed to prevent direct physical contact between the sensor wire and the patient, thereby allowing for the repeated use of the sensor wire in different patients. Because the sensor wire and system disclosed herein indicates the appropriate approach angle for penetration to the user before any actual penetration of tissue, the sensor wire enables the user to minimize inadvertent injury to neighboring tissue, such as, by way of non-limiting example, nerves, as the penetrating instrument travels toward the target structure.

The various figures show embodiments of devices, systems, and methods suitable to accurately locate and penetrate a vessel within a patient. One of ordinary skill in the art, however, would understand that similar embodiments could be used to locate and penetrate other anatomic structures without departing from the general intent or teachings of the present disclosure, including, but not limited to, gastrointestinal organs, sinuses, respiratory tracts, genitourinary organs, and adjacent structures.

FIG. 1 illustrates a cannulation system 100 according to one embodiment of the present disclosure. In the pictured embodiment, the cannulation system 100 includes a sensor wire 110 slidably disposed within a penetrating instrument 120, as well as a Doppler ultrasound system 125. The penetrating instrument 120 is shown in a cross-sectional view so that the sensor wire 110 can be seen inside the penetrating instrument 120. In the pictured embodiment, the Doppler ultrasound system 125 consists of a processor 130, an ultrasound pulse generator 135, a user input 138, and an indicating apparatus 140. The system 100 is arranged to facilitate the localization and penetration of an internal anatomic structure such as, by way of non-limiting example, a vessel. The individual component parts of the cannulation system 100 may be electrically, optically, and/or wirelessly connected to facilitate the transfer of power, signals, and/or data. The number and location of the components depicted in FIG. 1 are not intended to limit the present disclosure, and are merely provided to illustrate an environment in which the devices and methods described herein may be used.

In the illustrated embodiment, the sensor wire 110 is shaped and configured as an elongate, rigid, cylindrical tube. The sensor wire 110 includes a hollow elongate tube 145, a sensor 150, and a core wire 155. In one aspect, a core wire 155 extends between a proximal portion 160 and a distal portion 165 of the sensor wire 110. In the pictured embodiment, the sensor 150 is coupled to the core wire 155 at the distal portion 165. The sensor 150 may be attached to the core wire 155 or tube 145 in any of a variety of coupling mechanisms, including by way of non-limiting example, a snap-fit engagement, adhesive, welding, pressure fit, and/or mechanical fasteners. In the pictured embodiment, the sensor 150 is attached to the core wire 155 via welding and a housing around the sensor is bonded to the tube 145 via an adhesive. In a further embodiment, the sensor housing is directly attached to a rigid hollow elongate tube 145 and the core wire can be omitted, thereby forming a rigid sensor wire assembly. The sensor wire 110 will be described in further detail below with reference to FIGS. 4 and 5.

Figure 2:
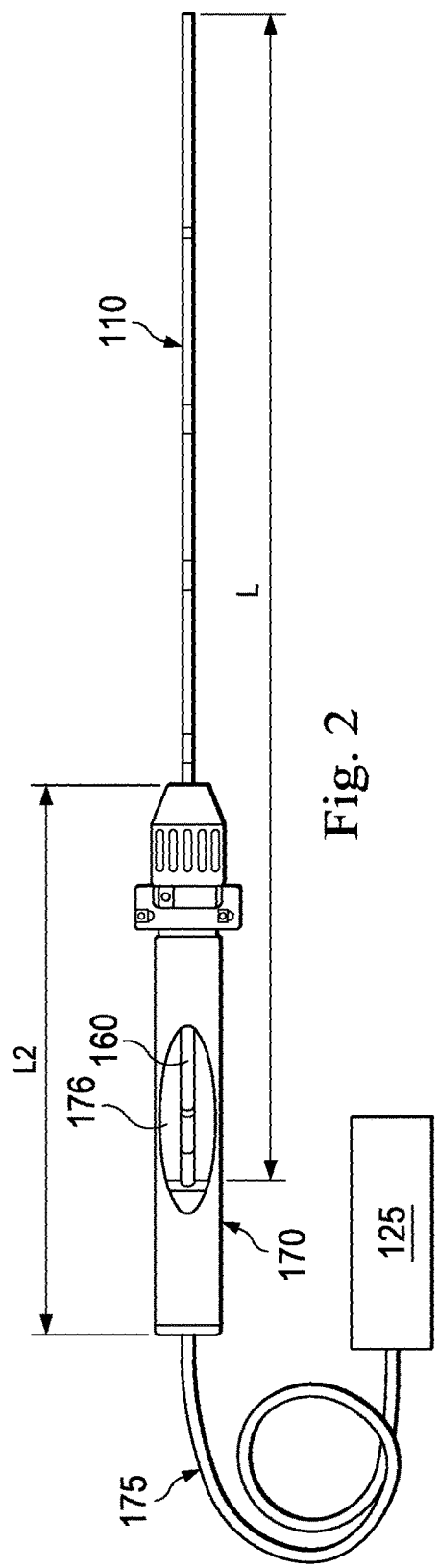
FIG. 2 illustrates a partial cutaway side-view of a sensor wire coupled to a connector according to one embodiment of the present disclosure.

The sensor wire 110 is coupled to the Doppler ultrasound system 125 in any of a variety of means known to those skilled in the art. In the pictured embodiment, the proximal portion 160 of the sensor wire 110 is coupled via a connector 170 to a supply cable 175 linked to the Doppler ultrasound system 125. In some embodiments, as shown in FIG. 2, the connector 170 has an inner passage 176 which can house the proximal portion 160 of the sensor wire 110. The sensor wire 110 may be selectively coupled to the connector 170 and the supply cable 175 in any of a variety of selective coupling mechanisms, including by way of non-limiting example, a threaded engagement, a snap-fit engagement, and a tension-based engagement. In some embodiments, the connector 170 comprises a handle sized such that it may be held and maneuvered by a user during a medical procedure. In the illustrated embodiment of FIG. 2, the connector is a conventional releasable connector utilized with coronary sensing systems sold by Volcano Corporation under the trade name ComboWire®. The sensor wire 110 possesses sufficient column strength to support the weight of the connector 170 without causing damage to or deformation of the sensor wire 110. In some embodiments, the connector 170 can be disconnected to allow the advancement of a surgical instrument, such as, by way of non-limiting example, a balloon catheter, an irrigation catheter, an imaging catheter, another suitable surgical catheter, another sensor wire, or a guidewire, over the sensor wire 110 or in place of the sensor wire 110. In some instances, the sensor wire and the connector include similar features to and interact in ways similar to those disclosed for the guidewire and connector, respectively, in U.S. Pat. No. 8,231,537, entitled "Combination Sensor Guidewire and Methods of Use" and filed on Jun. 23, 2006, which is hereby incorporated by reference in its entirety.

With reference to FIG. 1, the penetrating instrument 120 comprises an elongate, rigid tube. The penetrating instrument 120 includes a lumen 178 extending between a sharp distal tip 180 and a proximal end 185. The sharp distal tip 180 is shaped and configured to penetrate the skin, subcutaneous tissue, and other anatomic tissues of the patient (e.g., a vessel wall). In the pictured embodiment, the penetrating instrument 120 comprises a surgical needle. In other embodiments, the penetrating instrument may comprise a surgical introducer, which can be sized and shaped to allow the passage of the sensor wire 110 and/or other surgical instruments from the proximal end through the distal end. In other embodiments, as described below with reference to FIG. 10, the penetrating instrument may comprise the combination of a surgical introducer and a surgical needle, wherein the introducer is sized and shaped to allow the passage of the needle from a proximal end through a distal end, the needle is inserted into a lumen of the introducer, and the sensor wire is inserted into the needle.

The penetrating instrument 120 may range in an outer diameter D1 from 0.014 in (0.356 mm) to 0.040 in (1.016 mm). A wall thickness T of the penetrating instrument 120 may range from 0.001 to 0.004 inches. In one embodiment, the wall thickness T of the penetrating instrument is 0.002 in (0.051 mm). In one embodiment, the penetrating instrument 120 may be a conventional 20 gauge surgical needle. In another embodiment, the penetrating instrument may be a conventional 22 gauge surgical needle.

The sensor wire 110 extends through the lumen 178 of the penetrating instrument 120. The sensor wire 110 is shaped such that it can be slidably disposed within the lumen 178, and the sensor wire 110 is sized such that the distal portion 165 can extend beyond the distal tip 180 of the penetrating instrument 120. In other words, the sensor wire 110 is sized to be longer than the penetrating instrument 120. In the pictured embodiment, the diameter of the sensor wire 120 is sized to be less than the diameter of the lumen 178 of the penetrating instrument 120 to enable the sensor wire 110 to be reciprocally and axially moveable within the penetrating instrument 120. In particular, the penetrating instrument 120 and the sensor wire 110 are sized such that an outer diameter D2 of the sensor wire 110 is substantially equal to or less than an inner diameter D3 of the lumen 178 of the penetrating instrument 120. This enables reciprocating movement of the sensor wire 110 along a longitudinal axis LA within the lumen 178 in directions designated by arrows 187 and 188. The sensor wire 110 may range in diameter D2 from 0.008 in (0.203 mm) to 0.040 in (1.016 mm). For example, the sensor wire 110 may have any of a variety of diameters D2, including, by way of non-limiting example, 0.010 in (0.254 mm), 0.014 in (0.356 mm), and 0.035 in (0.889 mm). The penetrating instrument 120 may range in inner diameter D3 from 10 to 30 gauge. The penetrating instrument 120 may have any of a variety of inner diameters D3, including, by way of non-limiting example, 0.010 in (0.254 mm). With reference to FIG. 2, the sensor wire 110 may range in length L from 50 mm to 500 mm. For example, the sensor wire 110 may have any of a variety of lengths, including, by way of non-limiting example, 25 cm.

In one aspect, the connection assembly is significantly smaller in diameter in relation to the overall length. For example, in the illustrated embodiment, the length of the sensor wire 110 is greater than 100 times longer than the diameter of the communication connection assembly 113. In one example, it has about a 250:1 length to diameter ratio. The overall ratio of length to diameter is less than 1000:1 in the illustrated examples.

In another aspect, the length of the overall sensor wire 110 is less than 10 times longer than the length of the communication connection assembly 113. For example, the sensor wire 110 can have a length of approximately 25 cm while the connection assembly 113 has a length L3 of approximately 3 cm.

Referring to FIG. 2, the connector 170 is illustrated attached to a sensing wire 110. The connector 170 has a length L2. In one embodiment, L2 is about 5-15 cm in length. In still a further embodiment, L2 is 8-10 cm in length. The connector can range in lengths and orientation.

In some instances, the sensor wire 110 may be entirely removed in the proximal direction from the penetrating instrument 120. In other instances, the penetrating instrument 120 may be entirely removed in the proximal direction from around the sensor wire 110. For example, in some embodiments, the connector 170 may be disconnected from the sensor wire 110 to allow the removal of the penetrating instrument 120 in the proximal direction. When the user pierces the skin of a patient and advances the penetrating instrument 120 in order to reach the target vessel, the penetrating instrument 120 will pass through various neighboring tissues and fluids that may enter the lumen 178. In some embodiments, the outer diameter D2 of the sensor wire 110 closely approximates the inner diameter D3 of the lumen 178 of the penetrating instrument 120, such that the sensor wire 110 can block undesired aspiration of bodily fluids and/or other substances into the lumen 178 of the penetrating instrument 120 during a procedure. In instances where the outer diameter D2 of the sensor wire 110 is less than the inner diameter D3 of the lumen 178 of the penetrating instrument 120, other means for blocking such undesired aspiration may be used. For example, in some embodiments, the penetrating instrument includes a seal, such as, by way of non-limiting example, an O-ring, at the distal tip 180 to prevent or minimize the entry of such tissues and fluids into the lumen 178 as the penetrating instrument is advanced to the target vessel. In some embodiments, the penetrating instrument includes a conventional "bleed-back" chamber or valve. In some embodiments, the penetrating instrument is coupled to a Tuohy-Borst adapter to prevent backflow of fluid during insertion into a patient.

In the pictured embodiment, the penetrating instrument 120 includes a retaining feature 189 within the lumen 178 that prevents the sensor wire 110 from advancing a certain distance past the distal tip 180 and may selectively lock the sensor wire into position within the penetrating instrument. In some instances, the retaining feature 189 extends circumferentially around the inner lumen 178. The retaining feature 189 may comprise any of a variety of retaining mechanisms, including, by way of non-limiting example, a flexible O-ring, a mechanical coupling, and or an adhesive such as "soft glue." In some instances, the retaining feature 189 serves to center and/or align the sensor wire 110 with the distal tip 180 of the penetrating instrument 120. Other embodiments may have any number of retaining features. Some embodiments lack a retaining feature.

The Doppler ultrasound system 125 is configured for receiving, processing, and analyzing Doppler ultrasound data in accordance with one embodiment of the present disclosure. The Doppler ultrasound system 125 includes the processor 130, which is coupled to the ultrasound pulse generator 135 and the indicating apparatus 140. The Doppler ultrasound system 125 is coupled to the sensor wire 110, which carries the sensor 150. In the pictured embodiment, the sensor 150 comprises a Doppler ultrasound transducer. In some embodiments, the sensor 150 may comprise an array of transducers.

The processor 130 may include one or more programmable processor units running programmable code instructions for implementing the methods described herein, among other functions. The processor 130 may be integrated within a computer and/or other types of processor-based devices suitable for a variety of medical applications. The processor 130 can receive input data from the sensor wire 110 and/or the ultrasound pulse generator 135 directly via wireless mechanisms or from wired connections such as the supply cable 175. The processor 130 may use such input data to generate control signals to control or direct the operation of the sensor wire 110. In some embodiments, the user can program or direct the operation of the sensor wire 110 and/or the ultrasound pulse generator 135 from the user input 138. In some embodiments, the processor 130 is in direct wireless communication with the sensor wire 110, the ultrasound pulse generator 135, and/or the user input 138, and can receive data from and send commands to the sensor wire 110, the ultrasound pulse generator 135, and/or the user input 138.

In various embodiments, processor 130 is a targeted device controller that may be connected to a power source (not shown), accessory devices (such as, by way of non-limiting example, the indicating apparatus 140), and/or a memory (not shown). In such a case, the processor 130 is in communication with and performs specific control functions targeted to a specific device or component of the system 100, such as the sensor wire 110 and/or the ultrasound pulse generator 135, without utilizing input from the user input 138. For example, the processor 130 may direct or program the sensor wire 110 and/or the ultrasound pulse generator 135 to function for a specified period of time, at a particular frequency, and/or at a particular angle of incidence without specific user input. In some embodiments, the processor 130 is programmable so that it can function to simultaneously control and communicate with more than one component of the system 100. In other embodiments, the system 100 includes more than one processor and each processor is a special purpose controller configured to control individual components of the system.

The processor 130 is configured to acquire Doppler ultrasound data from a blood vessel through the sensor wire 110, and can analyze the data to determine the presence or absence and direction of fluid flow (e.g., blood flow) in front of the penetrating instrument 120. Doppler ultrasound measures the movement of objects through the emitted beam as a phase change in the received signal. When ultrasound waves are reflected from a moving structure (e.g., a red blood cell within a vessel), the wavelength and the frequency of the returning waves are shifted. If the moving structure is moving toward the transducer, the frequency increases. If the moving structure is moving away from the transducer, the frequency decreases. In some embodiments, the processor 130 employs the Doppler Equation $\Delta f=(2f_o V \cos \theta)/C$, where $\Delta f$ is the frequency shift, $f_o$ is the frequency of the transmitted wave, V is the velocity of the reflecting object (e.g., a red blood cell), $\theta$ is the angle between the incident wave and the direction of the movement of the reflecting object (i.e., the angle of incidence), and C is the velocity of sound in the medium. The frequency shift is maximal if the sensor 150 is oriented parallel to the direction of the blood flow and the $\theta$ is zero degrees (cos 0=1). The frequency shift is absent if the sensor 150 is oriented perpendicular to the direction of the blood flow and the $\theta$ is 90 degrees (cos 90=0). Higher Doppler frequency shifts are obtained the velocity is increased, the incident wave is more aligned to the direction of blood flow, and/or if a higher frequency is emitted.

In the pictured embodiment, the processor 130 is connected to the ultrasound pulse generator 135, and may control the ultrasound pulse generator. The ultrasound pulse generator 135 may comprise an ultrasound excitation or waveform generator that provides control signals (e.g., in the form of electric pulses) to the sensor wire 110 to control the ultrasound wave output from the sensor 150. In some instances, the ultrasound pulse generator 135 directs continuous wave ultrasound from the sensor 150, instead of pulsed wave ultrasound. In some instances, the ultrasound generator is part of the processor 130. In other instances, the ultrasound generator is integrated in the sensor wire 110.

In the pictured embodiment, the processor 130 is connected to the indicating apparatus 140, which is configured to convey information, including for example Doppler shift information gathered from the sensor wire 110, to the user. In some instances, the processor 130 creates an appropriate indication to display via the indicating apparatus 140. In some instances, the indicating apparatus 140 may be an oscillator or an auditory device configured to convey information to the user via auditory methods, such as meaningful tonality to convey different Doppler shift information. In other instances, the indicating apparatus 140 may convey different Doppler shift information via tactile sensations, including by way of non-limiting example, vibration. In other instances, as shown in FIG. 3, the indicating apparatus 140 may comprise a visual display configured to graphically or visually display the measured Doppler shifts to the user, and the average Doppler shift associated with different angles and/or positions of emitted energy may be displayed visually.

Figure 3:
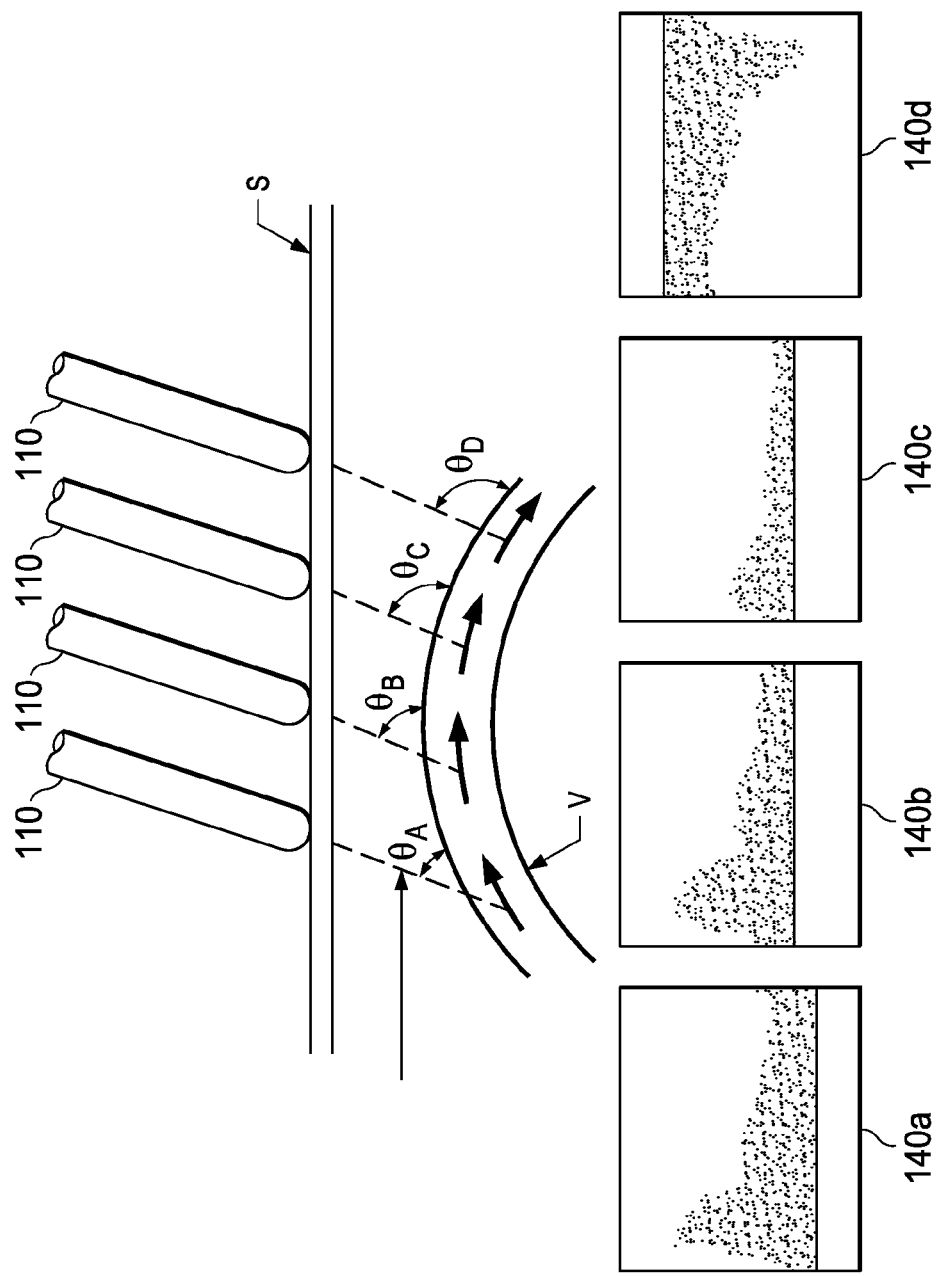
FIG. 3 is a diagram illustrating various angles of emitted Doppler ultrasound toward a vessel and the corresponding sonograms that result on an indicating apparatus according to one embodiment of the present disclosure.

In FIG. 3, the indicating apparatus displays various sonograms associated with the different Doppler shifts observed as the sensor wire 110 is moved across the skin S, thereby emitting ultrasound waves at different angles of incidence $\theta$ relative to the blood flow within the vessel V. At the angle of incidence $\theta A$, a higher-frequency Doppler signal is shown on the indicating apparatus 140a because the emitted beam is aligned more with the direction of flow within the vessel V. At the angle of incidence $\theta B$, a slightly lower-frequency Doppler signal is shown on the indicating apparatus 140b because the emitted beam is less aligned with the direction of flow within the vessel V. At the angle of incidence $\theta C$, a relatively poor Doppler signal is shown on the indicating apparatus 140c because the emitted ultrasound waves interact with the blood at almost 90 degrees. At the angle of incidence $\theta D$, a negative Doppler signal is shown on the indicating apparatus 140d because the blood is travelling away from the emitted ultrasound waves. In other embodiments, the Doppler shift information is displayed as color information superimposed on a background gray scale B mode ultrasound image. In some embodiments, a positive Doppler shift is assigned one color and a negative Doppler shift is assigned another color. In some embodiments, the magnitude of the Doppler shift is represented by the different gradients of brightness of the assigned color.

Figure 4:
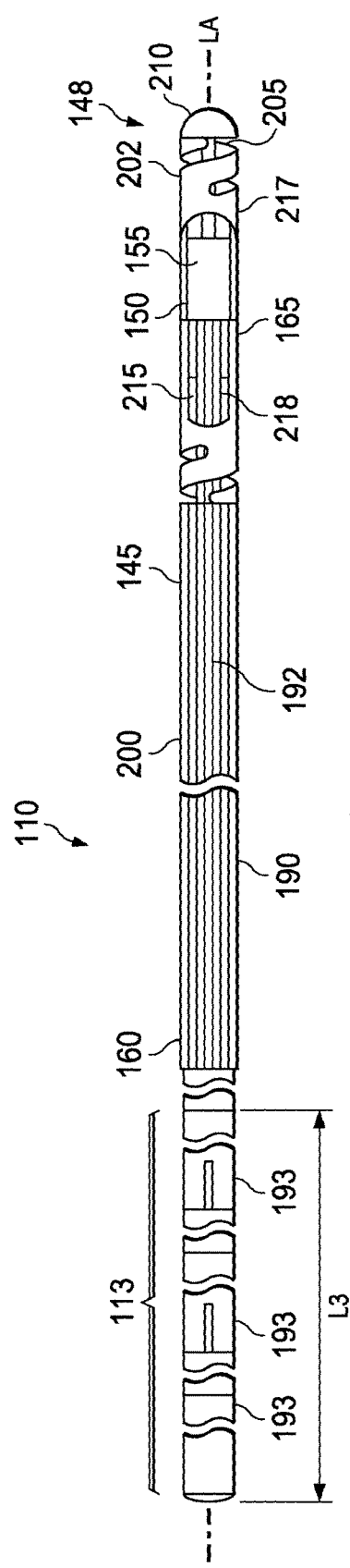
FIG. 4 illustrates a partial cutaway side-view of a sensor wire according to one embodiment of the present disclosure.

With reference to FIG. 4, as mentioned above, the sensor wire 110 comprises the elongate tube 145, and the sensor assembly 148 including a pressure sensor 150 and an ultrasound transducer 210. In the pictured embodiment, the elongate tube 145 is shaped as a rigid, hollow cylinder having a lumen 190 with a circular cross-sectional shape. With the rigid elongate tube, the sensor assembly 148, including the ultrasound sensor 210, are maintained in substantial alignment with the communication connection assembly 113 during use. The strength of the rigid elongate tube is sufficient to hold the weight of the female connector 170 along with the associated cable without substantially yielding from the longitudinal axis. However, in alternative embodiments, the elongate tube may be semi-rigid and partially flexible and allow the connection assembly 113 to be longitudinally offset from the sensor assembly 148. In various embodiments, the elongate tube can have any of a variety of cross-sectional shapes, including, for example, rectangular, square, or ovoid. The lumen 190 is shaped and sized to receive the core wire 155 and various electrical conductors 192 extending from the sensor assembly 148. The illustrated embodiment includes conductors extending to the pressure sensor 150 and conductors extending from the ultrasound transducer to the ultrasound energy supply (e.g., the supply cable 175 and the ultrasound pulse generator 135 (shown in FIG. 1)). Also depicted in the pictured embodiment are conductive bands 193 positioned at the proximal portion 160 of the sensor wire 110 forming a communication connection assembly 113. Various embodiments may include any number and arrangement of electrical conductors and conductive bands. Other embodiments may lack the electrical conductors 192 and/or the conductive bands 193.

As illustrated in FIG. 4, the connection assembly 113 has a substantially uniform diameter with each conductive band axially spaced coaxially along the longitudinal axis with matching outer diameters. The outer diameter of the connection assembly 113 substantially matches the outer diameter of the elongated tube 145 and sensor assembly 148. Thus, the sensor wire has a uniform outer diameter along its entire length. In addition to the alternatives set forth above, the outer diameter may be 0.0014 or 0.0018 inches in two alternative embodiments.

The elongate tube 145 may be composed of any of a variety of suitable biocompatible materials that are able to provide the desired amount of strength, rigidity, and corrosion resistance, including, by way of non-limiting example, Nitinol, stainless steel, titanium, nickel titanium alloys, cobalt alloys, combinations of tungsten/gold with stainless steel or cobalt alloys, alloys thereof, and polymers such as polyimide, polyetheretherketone (PEEK), polyamide, polyetherblockamide, polyethylene, polytetrafluoroethylene (PTFE), fluorinated ethylene propylene (FEP), and polyurethane. In some instances, the elongate tube 145 possesses sufficient column strength and resilience to support the weight of the connector 170 (shown in FIGS. 1 and 2) without causing damage to or deformation of the sensor wire 110. In the pictured embodiment, the elongate tube 145 possesses a substantially constant degree of stiffness along its length. In some instances, the sensor wire 110 has varying stiffness and flexibility along its length due to changes in material composition, thickness, and cross-sectional shape of the elongate tube 145.

An outer wall 200 of the elongate tube 145 may range in thickness from 1 mm to 40 mm. For example, the outer wall 200 may have any of a variety of thicknesses, including, by way of non-limiting example, 0.002 inches (0.051 mm). In some embodiments, the outer wall 200 may be treated or coated with a material to give the sensor wire 110 a smooth outer surface with low friction. In some embodiments, the sensor wire 110 is coated with a material along its length to ease insertion through the lumen 178 of the penetrating instrument 120. For example, the entire length of sensor wire 110 or a portion of its length may be coated with a material that has lubricating or smoothing properties. Exemplary coatings can be hydrophobic or hydrophilic. Typical coatings may be formed from, by way of non-limiting example, polytetraflouroethylene (PTFE) or Teflon™, a silicone fluid, or urethane-based polymers. Additionally or alternatively, other biocompatible coatings that provide the above mentioned properties could be used.

Figure 5:
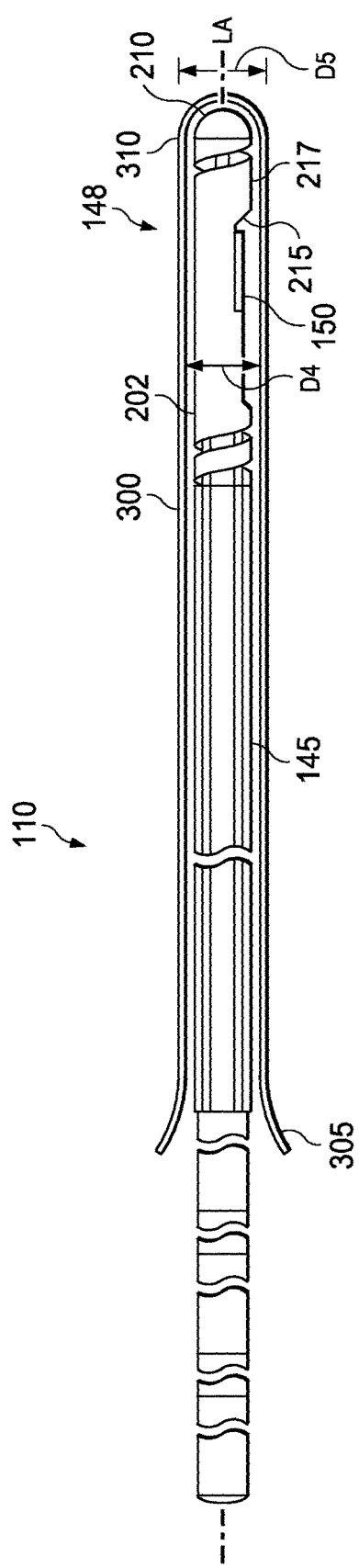
FIG. 5 illustrates a partial cutaway side-view of the sensor wire shown in FIG. 4 at a different angle and positioned within a sheath according to one embodiment of the present disclosure.

With reference to FIGS. 4 and 5, the distal tip including the ultrasound transducer 210 is shaped and configured as a blunt, atraumatic tip. In the pictured embodiment, the distal tip 210 is shaped as a rounded, hemispherical dome. In other embodiments, the distal tip may have any of a variety of atraumatic shapes, provided that the distal tip is configured to not penetrate the skin in the absence of undue pressure. In some embodiments, the distal tip 210 may be sufficiently flexible to eliminate the need for the curve of the tip to be atraumatic. In some embodiments where penetration of the skin by the sensor wire 110 is desired, the distal tip can be sharp and/or have angular edges.

The sensor 210 is shaped and configured to convey ultrasound energy along the longitudinal axis of the device through the distal tip. In particular, the sensor may be an ultrasound transducer configured to emit ultrasound waves and receive reflected ultrasound waves. In other embodiments, the sensor may comprise a separate ultrasound transmitter and receiver, wherein the transmitter and receiver may be communicatively coupled to each other via either a wired or wireless link. In the pictured embodiment, the sensor is shown as a single transducer. In alternative embodiments, the sensor may be any number of transducers, shaped in any of a variety of shapes and arranged in any of a variety of arrangements. In some embodiments, the sensor (and/or the sensor wire 110) includes additional amplifiers to achieve the desired sensitivity to the nature of the target fluid flow (e.g., blood flow and/or heart rate). It should also be appreciated that the sensor depicted herein is not limited to any particular type of sensor, and includes all Doppler sensors and/or ultrasonic transducers known to those skilled in the art. For example, a sensor wire having a single transducer adapted for rotation or oscillation, as well as a sensor wire having an array of transducers circumferentially positioned around the sensor wire are both within the spirit and scope of the present invention. In addition, the Doppler sensor may include an optical sensor.

In the illustrated embodiment, the sensing wire includes a pressure sensor 150. The pressure sensor can be used to sense the pressure of blood within the blood vessel once the introducer is inserted. In the blood is not above a predetermined pressure level, it may be an indicator that the introducer missed the vessel or entered a smaller vessel having too small of a diameter to receive the introducer.

FIG. 5 illustrates the sensor wire 110 shown in FIG. 4 rotated at a different angle about the longitudinal axis LA. In FIG. 5, the sensor wire 110 is shown partially surrounded or encased by a sheath 300. In some embodiments, the sensor wire 110 can be disposable in order to prevent the transfer of contagious diseases among different patients. In other embodiments, however, the sensor wire 110 may be reusable for performing medical procedures on different patients. If used with the sheath 300, for example, the sensor wire 110 can be reused on different patients because the probability of transferring a virus or bacterium among patients is reduced through the use of a disposable barrier such as the sheath 300. In other instances, the sensor wire 110 may be reused for procedures on different patients if it is sterilized between procedures.

In the pictured embodiment, the elongated, flexible, protective sheath 300 extends from a proximal end 305 to a distal end 310. The proximal end 305 is open and relatively larger in diameter than the closed distal end 310. In the pictured embodiment, the sheath 300 is transparent, and, in particular, transparent to ultrasound energy. The sheath 300 is designed to encase the sensor housing 202 and at least a portion of the elongate tube 145. In the pictured embodiment, the inner diameter D4 of the sheath 300 is slightly larger than the outer diameter D2 of the sensor wire 110 (shown in FIG. 1). An outer diameter D5 of the sheath 300 is slightly smaller than the inner luminal diameter D3 of the penetrating instrument 120 (shown in FIG. 1). Thus, the sensor wire 110, even when encased within the sheath 300, can move back and forth along the longitudinal axis LA within the lumen 198 of the penetrating instrument 120 (shown in FIG. 1).

Figure 6:
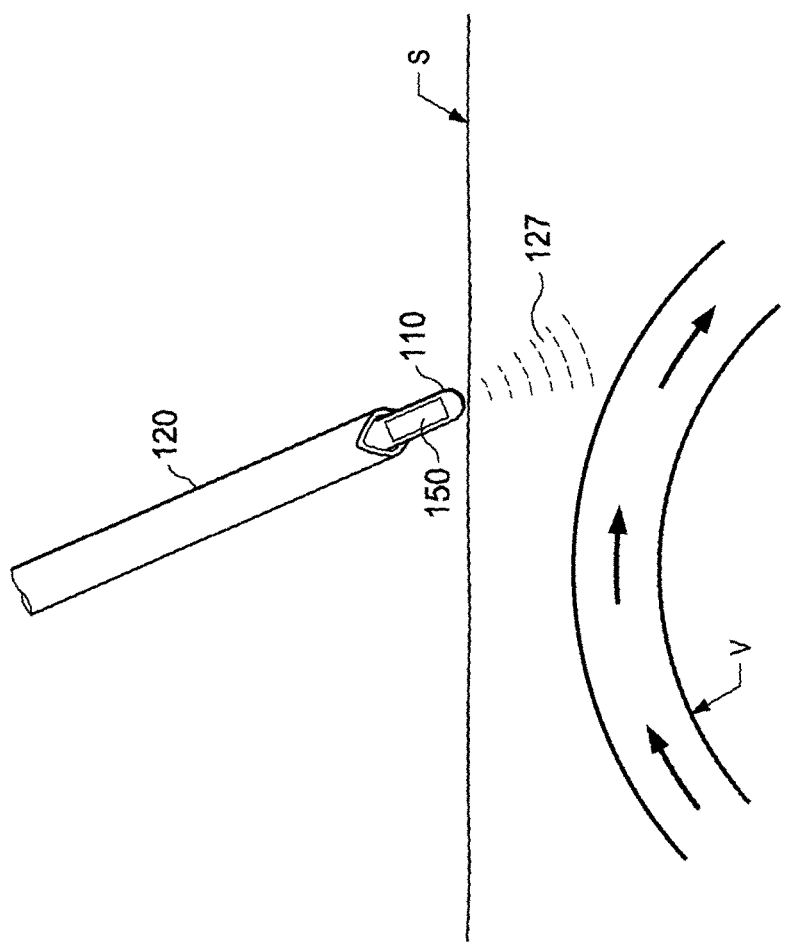
FIG. 6 is a schematic representation of a side view of the sensor wire disposed within the penetrating instrument and positioned against the skin of a patient according to one embodiment of the present disclosure.

FIG. 6 illustrates the sensor wire 110 disposed within the penetrating instrument 120 (e.g., prior to penetration of the skin S). In the pictured embodiment, the penetrating instrument 120 comprises a hollow bore needle. After threading the sensor wire 110 through the lumen 178 of the penetrating instrument 120, the user can advance the sensor wire 110 through the distal tip 180 of the penetrating instrument to position the sensor wire 110 against the skin S of a patient in the vicinity of a target vessel V. As mentioned above, the distal end 210 of the sensor wire 110 is shaped and configured to emerge from the distal tip 180 of the penetrating instrument 120 to contact the skin S. Once the sensor wire 110 is resting against the skin S, the user can activate the Doppler ultrasound system 125 to transmit ultrasound waves 127 from the sensor 150 through the skin S towards the vessel V. In some embodiments, the user may apply a liquid or gel material to the skin S to enhance the transmission and receipt of the ultrasound waves. The reflected signals obtained by the sensor 150 are communicated to the processor 130, which conveys the reflected data to the indicating apparatus 140 (shown in FIG. 1). If a Doppler shift is detected, the indicating apparatus 140 can convey the characteristics of the Doppler shift via an audible sound, a tactile sensation (e.g., a vibration), or a visual display. If the penetrating instrument is not directed toward the vessel V, the reflected Doppler signal will be weak or nonexistent. In FIG. 6, the reflected data shown on the indicating apparatus will reveal that the penetrating instrument is not located at an optimal angle and position to penetrate the vessel V. In some embodiments, the indicating apparatus 140 can indicate the direction of movement in which a user should move the penetrating instrument 120 to optimize the signal and locate the vessel V.

Figure 7:
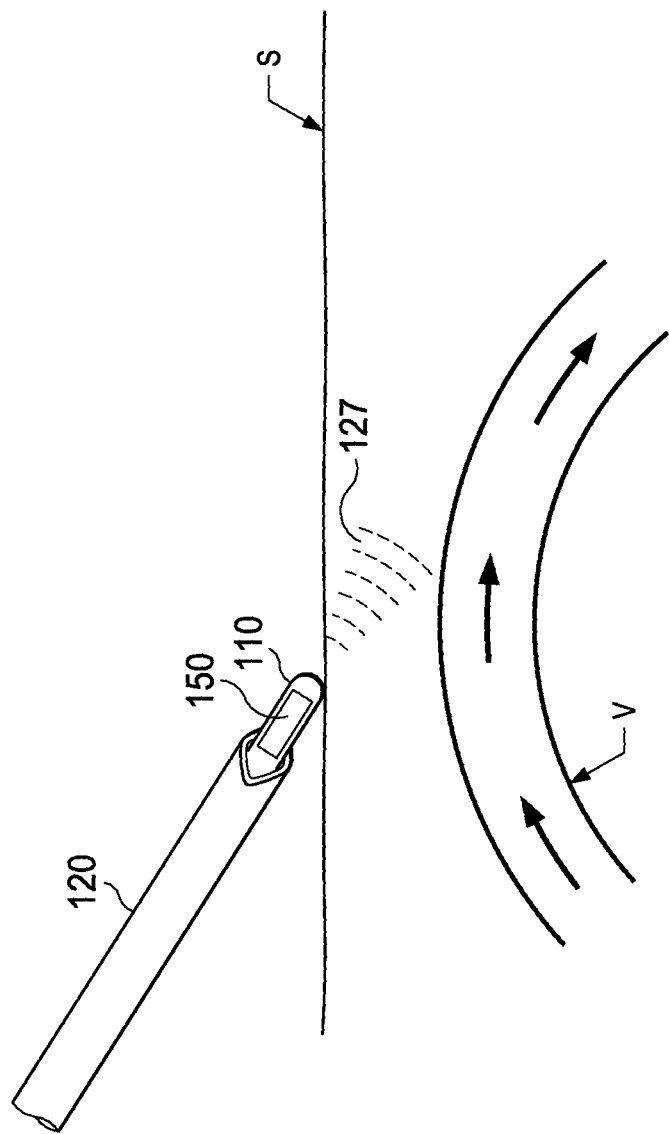
FIG. 7 is a schematic representation of a side view of the sensor wire disposed within the penetrating instrument and positioned against the skin of a patient in an optimal position to penetrate a vessel according to one embodiment of the present disclosure.

FIG. 7 illustrates a side view of the sensor wire 110 disposed within the penetrating instrument 120 and positioned against the skin S at a more optimal angle to penetrate the vessel V. As the user moves the penetrating instrument 120 and sensor wire 110 over the skin S and takes Doppler measurements, the indicating apparatus will continue to indicate the detected degree of Doppler shift. As the penetrating instrument 120 is directed toward the vessel V, and in particular toward the direction of flow within the vessel V, the reflected Doppler signals will increase in intensity. For example, when the user has moved the sensor wire 110 to the position shown in FIG. 7, the indicating apparatus 140 will reveal a Doppler shift indicating that the penetrating instrument 120 is located at an optimal angle and position to penetrate the vessel V.

Figure 8:
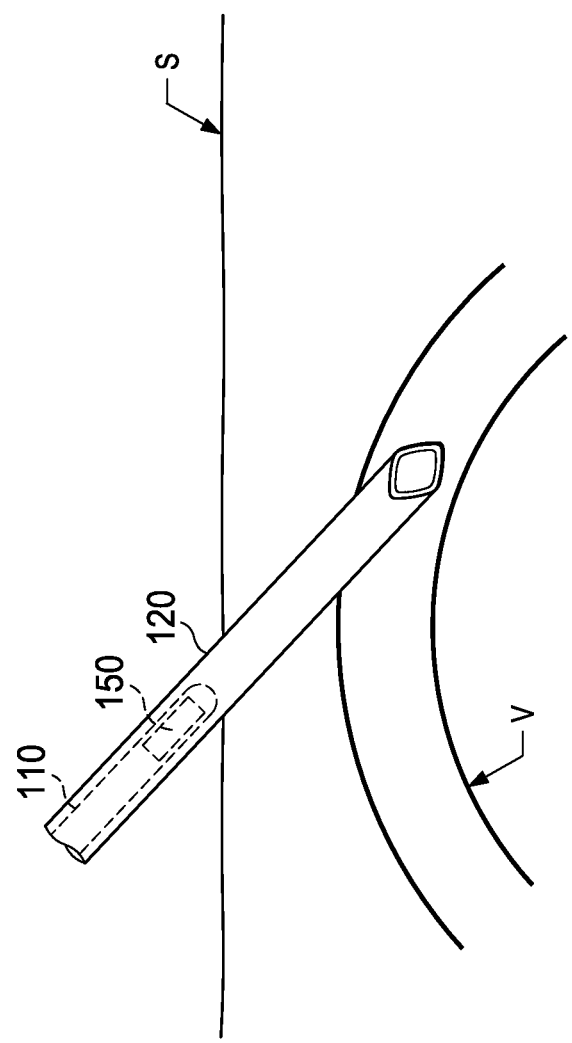
FIG. 8 is a schematic representation of a partially cross-sectional side view of the penetrating instrument advancing into a vessel while the sensor remains outside the skin of a patient according to one embodiment of the present disclosure.

FIG. 8 illustrates a partially cross-sectional side view of the penetrating instrument 120 advancing into the vessel V while the sensor wire 110 remains outside the skin S according to one embodiment of the present disclosure. Once the indicating apparatus 140 shows the user that the penetrating instrument 120 is optimally positioned to penetrate the vessel V, the user can advance the penetrating instrument 120 through the skin S and into the vessel V. Actual penetration of the vessel V may be indicated by back flow of the blood into the penetrating instrument 120 and/or a bleedback chamber or valve. In the pictured embodiment, the sensor wire 110 remains at the skin surface as the penetrating instrument 120 is advanced into the vessel V. In some embodiments, the user may manually prevent the sensor wire 110 from advancing with the penetrating instrument 120 by holding the sensor wire 110 in place proximal to the penetrating instrument 120 (e.g., by the connector 170 shown in FIGS. 1 and 2). In other embodiments, the sensor wire 110 may be temporarily restrained within the penetrating instrument by the connector 170 or by the retaining feature 189 within the lumen 178 of the penetrating instrument 120 (shown in FIG. 1). In some embodiments, the sensor wire 110 may be retracted and/or removed from the penetrating instrument 120 as the penetrating instrument is advanced into the vessel V.

Figure 9:
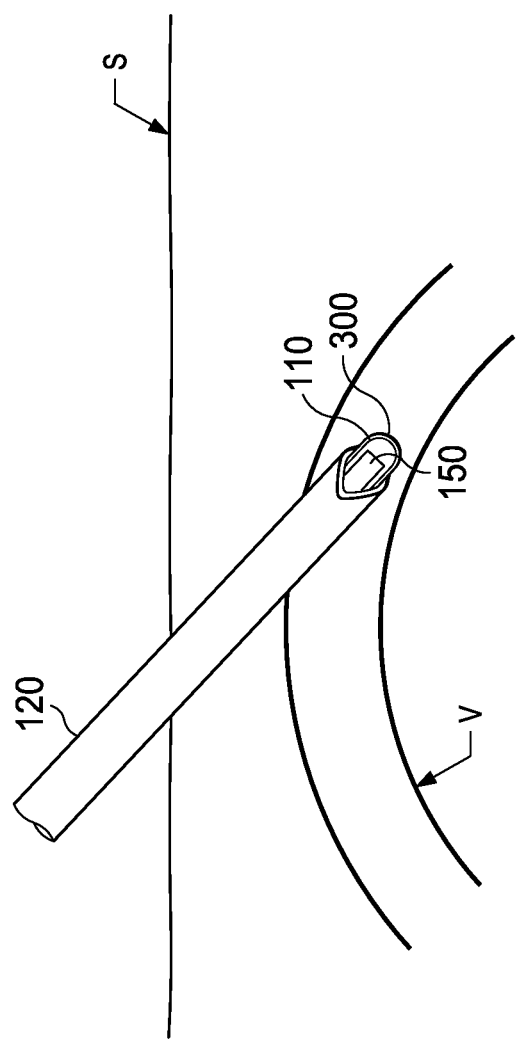
FIG. 9 is a schematic representation of a side view of the sensor wire encased in a sheath and disposed within the penetrating instrument, wherein both the sensor wire and the penetrating instrument are advancing into a vessel of a patient according to one embodiment of the present disclosure.

FIG. 9 is a schematic representation of a side view of the sensor wire 110 encased in the sheath 300 and disposed within the penetrating instrument 120, wherein both the sensor wire and the penetrating instrument are advanced into the vessel V according to one embodiment of the present disclosure. In this instance, the sensor wire 110 is inserted into the sheath 300 before being inserted into the penetrating instrument 120. The user can advance the sensor wire 110 and sheath 300 along with the penetrating instrument 120 into the vessel V without contaminating the sensor wire 110 (i.e., because the sheath 300 shields the sensor wire 110 from any tissue and fluid encountered within the patient). Actual penetration of the vessel V may be indicated by back flow of the blood into the penetrating instrument 120 and/or a bleedback chamber or valve. In some instances, actual penetration of the vessel V may be indicated by a stepped increase in the intensity of the reflected Doppler signal once the sensor wire 110 is within the vessel V. In such embodiments, if the sensor wire 110 is advanced into the vessel V, then the user can confirm the positioning of the penetrating instrument 120 within the vessel V before withdrawing the sensor wire 110 and sheath 300 from the patient.

Figure 10:
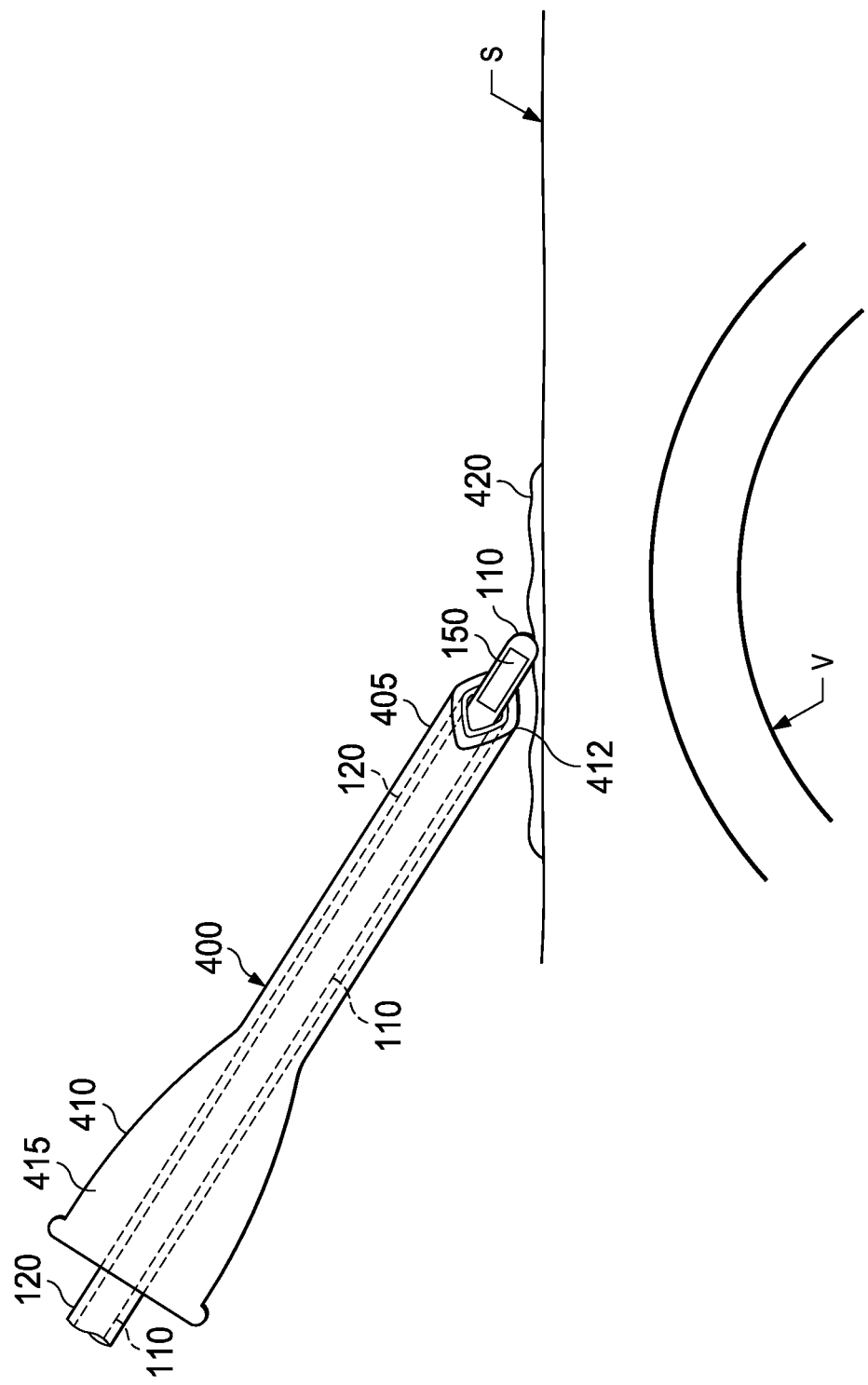
FIG. 10 is a schematic representation of a cross-sectional side view of the sensor wire disposed within the penetrating instrument and a delivery instrument, wherein the sensor wire is positioned against the skin of a patient according to one embodiment of the present disclosure.

FIG. 10 illustrates a cross-sectional side view of the sensor wire 110 disposed within the penetrating instrument 120 and a delivery instrument 400, wherein the sensor wire 110 is positioned against the skin S of a patient according to one embodiment of the present disclosure. In the pictured embodiment, the penetrating instrument 120 comprises a hollow bore needle, and the delivery instrument 400 comprises a protective sheath surrounding the needle. The delivery instrument 400 extends from a tapered distal portion 405 to a slightly flared proximal portion 410. In some embodiments, a distal tip 412 of the delivery instrument is sufficiently sharp to penetrate the skin S and the vessel V. In such embodiments, the delivery instrument 400 may function as the penetrating instrument 120, and the user may forego the use of a separate penetrating instrument. Instead, the user may thread the sensor wire 110 directly into a lumen 415 of the delivery instrument 400. In other embodiments, the distal tip 412 is blunt and atraumatic. The lumen 415 is sized and shaped to receive the penetrating instrument 120.

In the pictured embodiment, the user can pass the penetrating instrument 120 into the lumen 415 of the delivery instrument 400 before introducing the sensor wire 110 into the lumen 178 of the penetrating instrument 120. After threading the sensor wire 110 through the lumen 178 of the penetrating instrument 120, the user can advance the sensor wire 110 through the distal tip 180 of the penetrating instrument (and the distal portion 405 of the delivery instrument 400) to position the sensor wire 110 against the skin S of a patient in the vicinity of a target vessel V. As mentioned above, the distal end 210 of the sensor wire 110 is shaped and configured to emerge from the sharp distal tip 180 of the penetrating instrument 120 to contact the skin S.

Once the sensor wire 110 is resting against the skin S, the user can activate the Doppler ultrasound system 125 to transmit ultrasound waves from the sensor 150 through the skin S towards the vessel V. In some embodiments, the user may apply a liquid or gel material 420 to the skin S to enhance the transmission and receipt of the ultrasound waves. The reflected signals obtained by the sensor 150 are communicated to the processor 130, which conveys the reflected data to the indicating apparatus 140 (shown in FIG. 1). If a Doppler shift is detected, as described above in relation to FIG. 6, the indicating apparatus 140 can convey the characteristics of the Doppler shift via an audible sound, a tactile sensation (e.g., a vibration), or a visual display.

Figure 11:
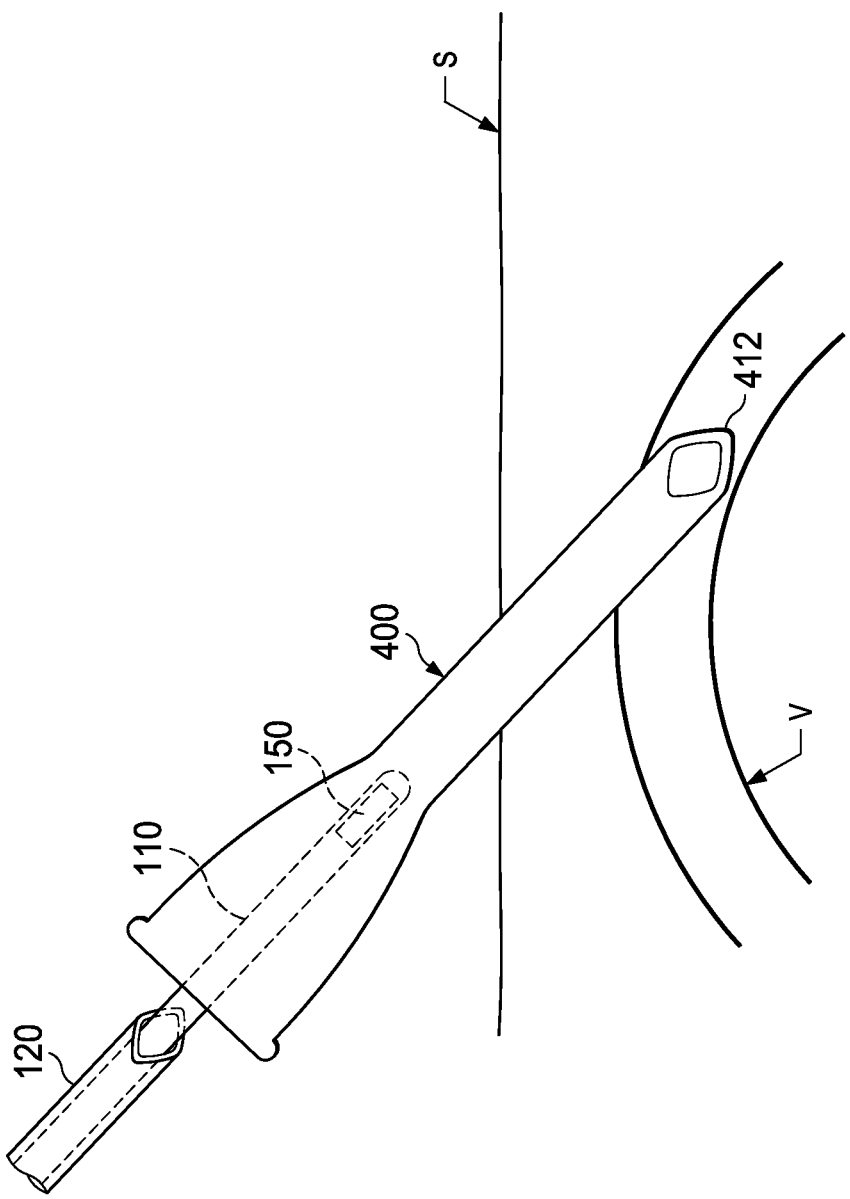
FIG. 11 is a schematic representation of a cross-sectional side view of the delivery instrument shown in FIG. 10 positioned within a vessel of a patient while the penetrating instrument and the sensor wire are being withdrawn according to one embodiment of the present disclosure.

FIG. 11 illustrates a cross-sectional side view of the delivery instrument 400 positioned within the vessel V while the penetrating instrument 120 and the sensor wire 110 are being withdrawn according to one embodiment of the present disclosure. Once the indicating apparatus 140 shows the user that the penetrating instrument 120 (and/or the delivery instrument 400) is optimally positioned to penetrate the vessel V, the user can advance the penetrating instrument 120 and the delivery instrument 400 through the skin S and into the vessel V. After withdrawal of the penetrating instrument 120 and the sensor wire 110, the delivery instrument 400 may be left within the vessel V to enable the introduction of other medical devices into the vessel V, such as the elongated sensing wire 1200 shown in FIG. 2.

FIG. 12 illustrates an intravascular sensing wire 1200 connected to the connector assembly 170 of the sensing system. The sensing wire includes a distal sensor 1202 that can include one or more sensors such as pressure, flow, temperature or imaging. The communication connection assembly 1260 on the proximal portion is configured to substantially match the outer diameter and length of the connection assembly 160 of the shorter access sensing wire. In one embodiment the two connection assemblies are identical in the number of electrical connectors, the diameter of the connectors and their axial spacing along the axis. In this form, both sensing wires may be sequentially received within the female lumen 176 of the connector 170. It is contemplated, that either of the sensor wires may include a different number of conductive bands, however, the spacing between bands must match the spacing of electrical contacts within the connector lumen 176. The sensing wire 1200 is a very flexible wire suitable for passing through a tortuous vascular route and can typically have a length from 75-200 cm. In most embodiments, the sensing wire length will be at least 10 times the length L2 of the connector 170

After the delivery instrument 400 has been positioned within the vessel V and access sensing wire removed, the distal end of the elongated sensing wire 1200 can be passed through the delivery instrument into the vessel. The elongated sensing wire can then be advanced from the initial vessel segment into other vessel segments of the vasculature of the patient. The proximal connection assembly 1260 can then be inserted into the lumen 176 of the connector 170 and the distal barrel rotated to lock the connection assembly in place. The sensing system can be utilized in a conventional fashion with the processing system receiving signals, analyzing the signals and providing an output to the user based on the sensed signals. Depending on the type of sensor 1202, the intravascular sensor can detect pressure, flow, temperature, or image a vessel segment spaced up to the length of the sensing wire away from the delivery instrument.

The cannulation system 100, which integrates the penetrating instrument 120 with the sensor wire 110 and the Doppler system 125, offers the user a faster and more accurate approach to vessel cannulation by allowing the user to accurately identify the optimal position and angle of penetration before puncturing the skin to access the target vessel. The system 100 not only enables the user to accurately penetrate the vessel without causing unnecessary damage to neighboring anatomic structures, but also enables the user to confirm the exact location of the penetrating instrument (and/or delivery instrument) within the vessel. Healthcare professionals will be able to access vessels much faster and more accurately using the system 100. The system can be particularly useful in patients having smaller or collapsed vessels (e.g., diabetic, elderly, pediatric, or obese patients).

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

I claim:

1. A device for locating a blood vessel in a patient, comprising:
   a hollow, elongate rigid tube including a lumen extending from a proximal portion to a distal portion, the tube having a longitudinal axis, the tube positionable at a plurality of angles with respect to the vessel;
   an ultrasonic sensor disposed within the tube, and slidably coupled to the tube, wherein the ultrasonic sensor transmits ultrasound waves coaxially with the longitudinal axis and receives ultrasound waves distally along the longitudinal axis to detect Doppler shift, and wherein the ultrasonic sensor is configured to determine, from a position outside the patient's body, whether the tube is positioned at a desired angle of the plurality of angles for entry into the vessel;
   at least one communication line extending from the ultrasonic sensor to a communication connection assembly positioned adjacent to the proximal portion; and electrical conductors in communication with the ultrasonic sensor extending through the lumen of the elongate tube.

2. The device of claim 1, wherein the tube is a rigid cylinder with a circular cross-sectional shape.

3. The device of claim 1, wherein the communication connection assembly includes a plurality of conductive bands on the proximal portion of the tube.

4. The device of claim 1, wherein the tube has a substantially constant degree of stiffness from the proximal portion to the distal portion.

5. The device of claim 1, wherein the tube and communication connection assembly have a substantially uniform diameter.

6. The device of claim 1, further including a sensor housing shaped and configured to enclose the ultrasonic sensor, wherein the sensor housing is coupled to the distal portion of the tube.

7. The device of claim 6, wherein the sensor housing includes a blunt, rounded distal tip.

8. The device of claim 6, wherein the sensor housing includes an ultrasonically- transparent aperture through which the ultrasonic sensor can transmit and receive ultrasound waves.

9. The device of claim 6, wherein the sensor housing comprises a steerable tip.

10. The device of claim 6, wherein the sensor housing includes a sharp distal tip.

11. The device of claim 1 further comprising at least one pressure sensor.

12. The device of claim 6, further including a flexible sheath shaped and configured to surround the sensor housing and at least the distal portion of the tube, the sheath having a closed distal end and an open proximal end.

13. The device of claim 12, wherein the flexible sheath tapers from the proximal end to the distal end.

14. The device of claim 12, wherein the flexible sheath is transparent to ultrasound energy.

* * * * *